United States Patent [19]

Jensen-Korte et al.

[11] Patent Number: 4,804,675
[45] Date of Patent: Feb. 14, 1989

[54] 1-ARYL-4-ALKYLTHIOPYRAZOL-5-AMINE DERIVATIVES, COMPOSITION CONTAINING THEM, AND METHOD OF USING THEM TO COMBAT INSECTS, ARACHNIDS, AND NEMATODES

[75] Inventors: Uta Jensen-Korte, Duesseldorf; Reinhold Gehring, Wuppertal; Otto Schallner, Monheim; Jörg Stetter, Wuppertal; Heinz-Jürgen Wroblowsky, Langenfeld; Benedikt Becker, Mettmann; Bernhard Homeyer, Leverkusen; Wolfgang Behrenz, Overath-Steinenbrück; Wilhelm Stendel; Peter Andrews, both of Wuppertal, all of Fed. Rep. of Germany

[73] Assignee: Bayer Aktiengesellschaft, Leverkusen, Fed. Rep. of Germany

[21] Appl. No.: 858,475

[22] Filed: Apr. 30, 1986

[30] Foreign Application Priority Data

May 17, 1985 [DE] Fed. Rep. of Germany ....... 3517843
Jan. 30, 1986 [DE] Fed. Rep. of Germany ....... 3602728

[51] Int. Cl.$^4$ .................... A01N 43/56; C07D 231/44
[52] U.S. Cl. .................................. 514/407; 514/341; 546/279; 548/362
[58] Field of Search ................ 548/362; 514/407, 341; 546/279

[56] References Cited

U.S. PATENT DOCUMENTS 4,589,905  5/1986  Beck ..................................... 546/279
4,614,533  9/1986  Schallner et al. .................... 548/362
4,620,865 11/1986  Beck et al. ............................. 71/92

Primary Examiner—Mary C. Lee
Assistant Examiner—Kurt G. Briscoe
Attorney, Agent, or Firm—Sprung Horn Kramer & Woods

[57] ABSTRACT

A method of combating insects, sense animals and nematodes comprising applying to insects, arachnids and nematodes and/or their environment an effective amount of at least one 5-aminopyrazole of the formula (I)

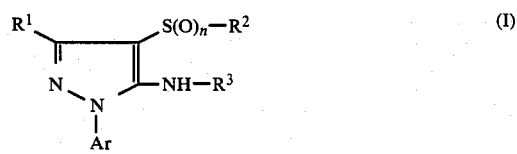

in which
$R^1$ represents hydrogen, alkyl or halogenoalkyl,
$R^2$ represents alkyl, halogenoalkyl, unsubstituted or substituted aralkyl or unsubstituted or substituted aryl,
$R^3$ represents hydrogen, alkyl or a radical

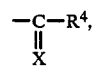

Ar represents unsubstituted or substituted phenyl or unsubstituted or substituted pyridyl and
n represents the number 0, 1 or 2,
wherein
X represents oxygen or sulphur and
$R^4$ represents hydrogen, alkyl, alkenyl, alkinyl, halogenoalkyl, alkoxyalkyl, alkylthioalkyl, unsubstituted or substituted cycloalkyl, unsubstituted or substituted aryl, alkoxy, alkylthio, unsubstituted or substituted aryloxy, unsubstituted or substituted arylthio, alkylamino, dialkylamino or unsubstituted or substituted arylamino.

11 Claims, No Drawings

1-ARYL-4-ALKYLTHIOPYRAZOL-5-AMINE DERIVATIVES, COMPOSITION CONTAINING THEM, AND METHOD OF USING THEM TO COMBAT INSECTS, ARACHNIDS, AND NEMATODES

The invention relates to the use of 5-aminopyrazole derivatives, some of which are known, as agents for combating pests, in particular as insecticides, acaricides and nematicides.

It is already known that pyrazole derivatives, such as, for example, 1,4-dimethyl-5-[N,N-(dimethyl)carbamoyloxy]-3-methylthiomethyl-pyrazole or 5-[N,N-(dimethyl)-carbamoyloxy]-1-methyl-3-methylsulphinyl-methylpyrazole or 5-[N,N-(dimethyl)-carbamoyloxy]-1-isopropyl-3-methylsulphonylmethyl-pyrazole or 5-[N,N-(dimethyl)-carbamoyloxy]-1-isobutyl-5-[N,N-(dimethyl)-carbamoylox]-3-methylthiomethylpyrazole or 1-cyclohexyl-5-[N,N-(dimethyl)carbamoyloxy]-3-methylsulphonyl-pyrazole, have an insecticidal, nematicidal and fungicidal action. (Compare DE-OS (German Published Specification) No. 2,819,932; DE-OS (German Published Specification) No. 2,839,270 or DE-OS (German Published Specification) No. 2,912,494).

However, the level of action and the duration of action of these compounds are not always completely satisfactory, especially against certain insects or when low concentrations are used.

It is also known that certain coumarinyl-phosphoric acid esters, such as, for example, O,O-diethyl O-(3-chloro-4-methyl-coumarin-7-yl) thionophosphate, exhibit a very good action against certain ectoparasites (compare, for example, "Pflanzenschutz und Schädlingsbekämpfung" (Plant protection and combating pests") K.H. Büchel, G. Thieme Verlag Stuttgart 1977, page 38).

However, the activity of this class of compound is also not always completely satisfactory, especially in the case of low application amounts and concentrations.

Finally, certain 5-amino-1-aryl-pyrazoles are known (compare, for example, Pharmaco, Ed. Sci. 26, 276-293 [1971] or Mycopathologica 74, 7-14 [1981] and C.A. 96; 1964 llj, and C.A. 95; 36257 q).

However, nothing is yet known of an activity of this class of compound towards insects, mites or nematodes.

It has been found that the 5-aminopyrazoles, some of which are known, of the general formula (I)

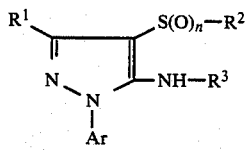

in which
R¹ represents hydrogen, alkyl or halogenoalkyl,
R² represents alkyl, halogenoalkyl, optionally substituted aralkyl or optionally substituted aryl,
R³ represents hydrogen, alkyl or a radical

Ar represents in each case optionally substituted phenyl or pyridyl and
n represents the number 0, 1 or 2,
wherein
X represents oxygen or sulphur and
R⁴ represents hydrogen, alkyl, alkenyl, alkinyl, halogenoalkyl, alkoxyalkyl, alkylthioalkyl, optionally substituted cycloalkyl, optionally substituted aryl, alkoxy, alkylthio, optionally substituted aryloxy, optionally substituted arylthio, alkylamino, dialkylamino or optionally substituted arylamino,
have insecticidal, acaricidal and nematicidal properties.

Surprisingly, the 5-aminopyrazoles of the general formula (I) to be used according to the invention exhibit a considerably improved insecticidal, acaricidal and nematicidal activity than the pyrazole derivatives known from the prior art, such as, for example, 1,4-dimethyl-5-[N,N-(dimethyl)-carbamoyloxy]-3-methyl-thiomethyl-pyrazole or 5-[N,N-(dimethyl)-carbamoyloxy]-1-methyl-3-methylsulphinylmethyl-pyrazole or 5-[N,N-(dimethyl)-carbamoyloxy]-1-isopropyl-3-methylsulphinylmethyl-pyrazole or 5-[N,N-(dimethyl)-carbamoyloxy]-1-isobutyl-3-methyl-sulphinylmethylpyrazole or 1-cyclohexyl-5-[N,N-(dimethyl)-carbamoyloxy]-3-methylthiomethyl-pyrazole or 1-cyclohexyl-5-[N,N-(dimethyl)-carbamoyloxy]-3-methylsulphinyl-pyrazole or 1-cyclohexyl-5-[N,N-(dimethyl)-carbamoyloxy]-3-methylsulphonylpyrazole, or the coumarinyl-phosphoric acid esters known from the prior art, such as for example O,O-diethyl O-(3-chloro-4-methyl-coumarin-7-yl) thionophosphate, which are closely related compounds chemically and-/or from the point of view of their action.

Formula (I) provides a general definition of the 5-aminopyrazole derivatives to be used according to the invention. Preferred compounds of the formula (I) are those in which R¹ represents in each case straight-chain or branched alkyl or halogenoalkyl with 1 to 4 carbon atoms and, where appropriate, 1 to 9 identical or different halogen atoms, or represents hydrogen, R² represents in each case straight-chain or branched alkyl or halogenoalkyl with in each case 1 to 8 carbon atoms and, where appropriate, 1 to 17 identical or different halogen atoms, or represents phenyl or phenylalkyl with, where appropriate, 1 to 4 carbon atoms in the straight-chain or branched alkyl part and in each case optionally monosubstituted or polysubstituted by identical or different substituents, possible substituents on the phenyl in each case being: halogen, cyano, nitro and in each case straight-chain or branched alkyl, alkoxy, alkylthio, alkylsulphinyl, alkylsulphonyl, halogenoalkyl, halogenoalkoxy, halogenoalkylthio, halogenoalkylsulphinyl and halogenoalkylsulphonyl with in each case 1 to 4 carbon atoms in the individual alkyl parts and, where appropriate, 1 to 9 identical or different halogen atoms, R³ represents hydrogen, straight-chain or branched alkyl with 1 to 4 carbon atoms or a radical

wherein
X represents oxygen or sulphur and
R⁴ represents hydrogen, or represents in each case straight-chain or branched alkyl, alkenyl, alkinyl, alkoxyalkyl, alkylthioalkyl, alkoxy, alkylthio, alkylamino, dialkylamino or halogenoalkyl with in each case up to 4 carbon atoms in the individual alkyl parts and, in the case of halogenoalkyl, with up to 9 identical or different halogen atoms, or represents cycloalkyl which has 3 to 7 carbon atoms and is optionally monosubstituted or polysubstituted by identical or different substituents from the group comprising halogen, lower alkyl and lower halogenoalkyl, or represents phenyl, phenoxy, phenylthio or phenylamino, in each case optionally monosubstituted or polysubstituted by identical or different substituents, possible substituents on the phenyl being those mentioned in the case of $R^2$, Ar represents phenyl, 2-pyridyl, 3-pyridyl or 4-pyridyl, in each case optionally monosubstituted or polysubstituted by identical or different substituents, possible substituents being: cyano, nitro, halogen, in each case straight-chain or branched alkyl, alkoxy and alkoxycarbonyl with in each case up to 4 carbon atoms, in each case straight-chain or branched halogenoalkyl and halogenoalkoxy with in each case up to 4 carbon atoms and up to 9 identical or different halogen atoms and a radical —S(O)$_m$—R$^5$ wherein
$R^5$ represents amino, or represents in each case straight-chain or branched alkyl, alkylamino, dialkylamino or halogenoalkyl with in each case up to 4 carbon atoms in the individual alkyl parts and, in the case of the halogenoalkyl, with up to 9 identical or different halogen atoms, and m represents the number 0, 1 or 2, and
n likewise represents the number 0, 1 or 2.

Particularly preferred compounds of the formula (I) are those in which $R^1$ represents hydrogen, methyl, ethyl, n- or i-propyl or trifluoromethyl, $R^2$ represents methyl, ethyl, n- or i-propyl, n-, i-, s- or t-butyl, n- or i-pentyl, n- or i-hexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl or chloropropyl, or represents phenyl, benzyl or phenethyl, in each case optionally mono-, di- or trisubstituted by identical or different substituents, possible substituents on the phenyl being: fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl and trifluoromethylsulphonyl, $R^3$ represents hydrogen, methyl, ethyl or n- or i-propyl, or represents a radical

wherein
X represents oxygen or sulphur and
$R^4$ represents hydrogen, methyl, ethyl, n- or i-propyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromomethyl, 3-chloropropyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl and trifluoromethyl, or represents phenyl, phenoxy, phenylthio or phenylamino, in each case optionally mono-, di- or trisubstituted by identical or different substituents from the group comprising methyl, methoxy, chlorine or trifluoromethyl, Ar represents phenyl, 2-pyridyl, 3-pyridyl or 4-pyridyl, in each case optionally mono-, di-, tri-, tetra- or pentasubstituted by identical or different substituents, possible substituents being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)$_m$—R$^5$, wherein
$R^5$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, m represents the number 0, 1 or 2 and
n likewise represents the number 0, 1 or 2.

The following 5-aminopyrazoles of the general formula (I) may be mentioned specifically, in addition to the compounds mentioned in the preparation examples:

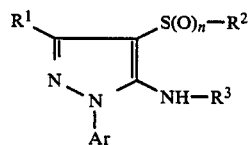

| $R^1$ | $R^2$ | $R^3$ | n | Ar |
|-------|-------|-------|---|----|
| CH$_3$ | CH$_3$ | H | 0 |  |
| CH$_3$ | CH$_3$ | H | 1 |  |

-continued
| R¹ | R² | R³ | n | Ar |
|---|---|---|---|---|
| CH₃ | CH₃ | —CO—C₂H₅ | 2 | 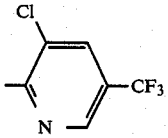 |
| CF₃ | CH₃ | H | 0 | 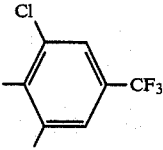 |
| CF₃ | CF₃ | H | 0 | 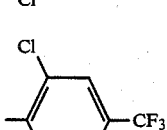 |
| CF₃ | CCl₂F | H | 0 | 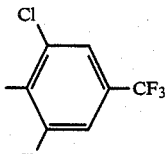 |
| CF₃ | CClF₂ | H | 0 | 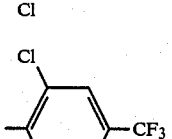 |
| CF₃ | C₂H₅ | H | 0 | 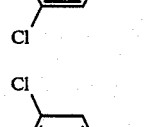 |
| CF₃ | CH₃ | H | 1 | 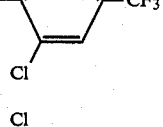 |
| CF₃ | CF₃ | H | 1 | 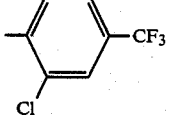 |
| CF₃ | CCl₂F | H | 1 | 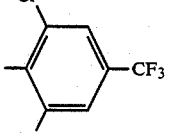 |
-continued
| R¹ | R² | R³ | n | Ar |
|---|---|---|---|---|
| CF₃ | C₂H₅ | H | 1 |  |
| CF₃ | CH₃ | H | 2 | 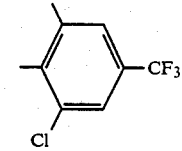 |
| CF₃ | CF₃ | H | 2 | 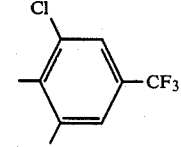 |
| CF₃ | CCl₂F | H | 2 | 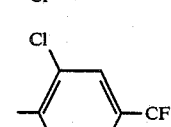 |
| CF₃ | CFCl₂ | H | 2 | 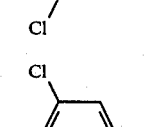 |
| CF₃ | C₂H₅ | H | 2 | 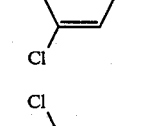 |
| CH₃ | CH₃ | H | 0 | 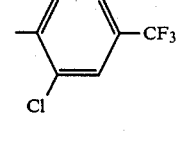 |
| CH₃ | C₂H₅ | H | 0 | 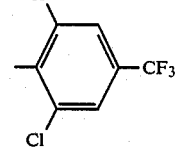 |
| CH₃ | CH₃ | H | 1 | 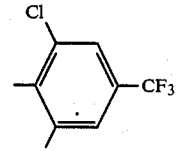 |

-continued
| R¹ | R² | R³ | n | Ar |
|---|---|---|---|---|
| CH₃ | CH₃ | H | 2 | 2,6-dichloro-4-(trifluoromethyl)phenyl 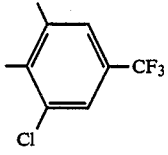 |
| CH₃ | C₂H₅ | H | 1 | 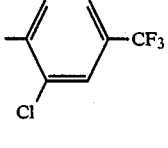 |
| CH₃ | C₂H₅ | H | 2 | 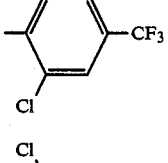 |
| CH₃ | CF₂Cl | H | 0 | 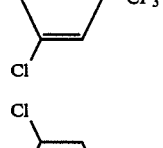 |
| CH₃ | CF₂Cl | H | 1 | 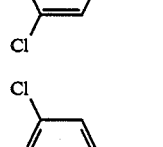 |
| CH₃ | CF₂Cl | H | 2 | 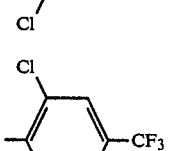 |
| CH₃ | CF₃ | H | 1 | 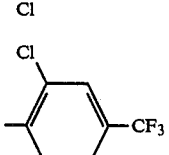 |
| CH₃ | CF₃ | H | 2 | 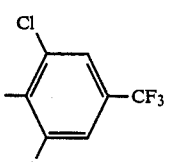 |
| CH₃ | CCl₂F | H | 1 |  |
-continued
| R¹ | R² | R³ | n | Ar |
|---|---|---|---|---|
| CH₃ | CCl₂F | H | 2 | 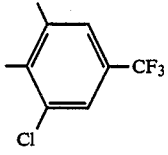 |
| H | CF₃ | H | 0 | 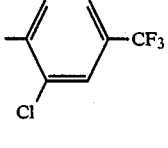 |
| H | CF₃ | H | 1 | 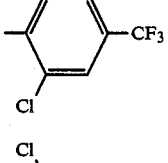 |
| H | CF₃ | H | 2 | 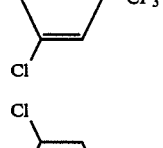 |
| H | CCl₂F | H | 0 | 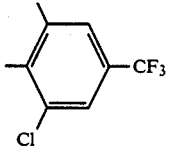 |
| H | CCl₂F | H | 1 | 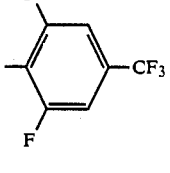 |
| H | CCl₂F | H | 2 | 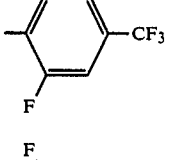 |
| H | CF₂Cl | H | 0 | 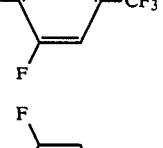 |
| H | CF₂Cl | H | 1 | 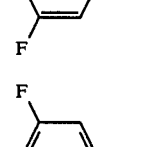 |

-continued
| R¹ | R² | R³ | n | Ar |
|---|---|---|---|---|
| H | CF₂Cl | H | 2 | 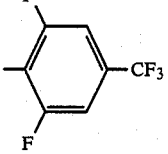 |
| CH₃ | CF₃ | H | 0 | 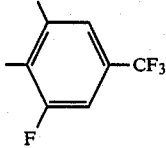 |
| CH₃ | CF₃ | H | 1 | 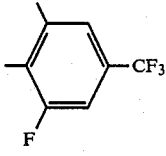 |
| CH₃ | CF₃ | H | 2 | 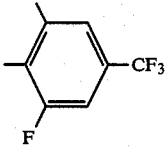 |
| CH₃ | CCl₂F | H | 0 | 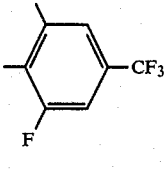 |
| CH₃ | CCl₂F | H | 1 | 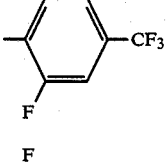 |
| CH₃ | CCl₂F | H | 2 | 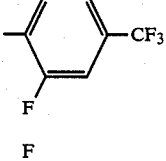 |
| H | CH₃ | H | 0 | 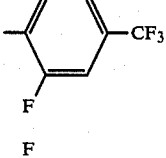 |
| H | CH₃ | H | 1 | 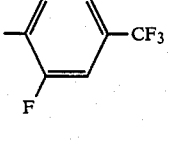 |
-continued
| R¹ | R² | R³ | n | Ar |
|---|---|---|---|---|
| H | CH₃ | H | 2 | 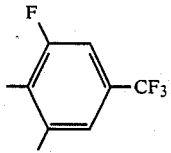 |
| H | C₂H₅ | H | 0 | 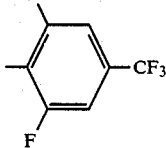 |
| H | C₂H₅ | H | 1 | 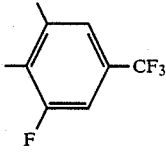 |
| H | C₂H₅ | H | 2 | 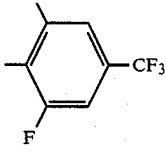 |
| H | CF₃ | H | 0 | 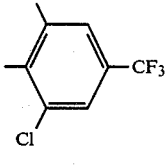 |
| H | CF₃ | H | 1 | 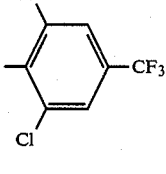 |
| H | CF₃ | H | 2 | 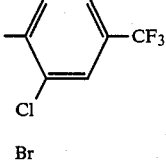 |
| H | CCl₂F | H | 0 | 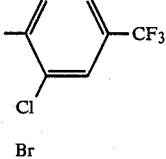 |
| H | CCl₂F | H | 1 | 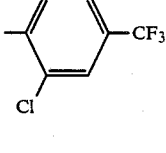 |

4,804,675

-continued

| R¹ | R² | R³ | n | Ar |
|---|---|---|---|---|
| H | CCl₂F | H | 2 | 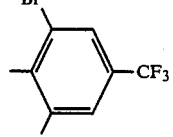 4-CF₃, 2-Br, 6-Cl phenyl |
| CH₃ | CH₃ | H | 0 | 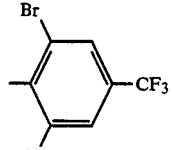 4-CF₃, 2-Br, 6-Cl phenyl |
| CH₃ | CH₃ | H | 1 | 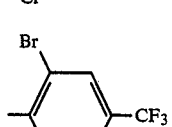 4-CF₃, 2-Br, 6-Cl phenyl |
| CH₃ | CH₃ | CH₃ | 2 | 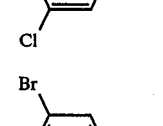 4-CF₃, 2-Br, 6-Cl phenyl |
| CH₃ | CCl₂F | H | 0 | 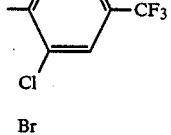 4-CF₃, 2-Br, 6-Cl phenyl |
| CH₃ | CCl₂F | H | 1 | 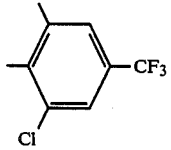 4-CF₃, 2-Br, 6-Cl phenyl |
| CH₃ | CCl₂F | H | 2 | 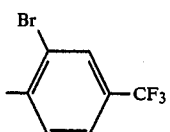 4-CF₃, 2-Br, 6-Cl phenyl |
| CH₃ | CF₃ | H | 0 | 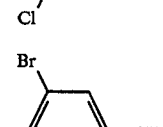 4-CF₃, 2-Br, 6-Cl phenyl |
| CH₃ | CF₃ | H | 1 | 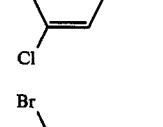 4-CF₃, 2-Br, 6-Cl phenyl |

-continued

| R¹ | R² | R³ | n | Ar |
|---|---|---|---|---|
| CH₃ | CF₃ | H | 2 | 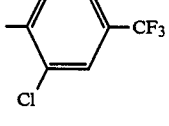 4-CF₃, 2-Br, 6-Cl phenyl |
| CH₃ | CF₃ | H | 0 | 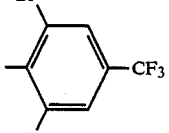 4-OCF₃, 2,6-diCl phenyl |
| CH₃ | CF₃ | H | 1 |  4-OCF₃, 2,6-diCl phenyl |
| CH₃ | CF₃ | H | 2 |  4-OCF₃, 2,6-diCl phenyl |
| CH₃ | CCl₂F | H | 0 | 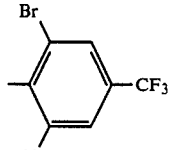 4-OCF₃, 2,6-diCl phenyl |
| CH₃ | CCl₂F | H | 1 | 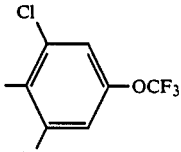 4-OCF₃, 2,6-diCl phenyl |
| CH₃ | CCl₂F | H | 2 | 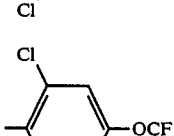 4-OCF₃, 2,6-diCl phenyl |
| H | CH₃ | H | 0 | 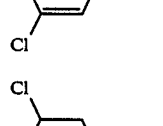 4-OCF₃, 2,6-diCl phenyl |
| H | CH₃ | H | 1 | 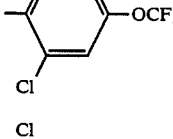 4-OCF₃, 2,6-diCl phenyl |

-continued

| R¹ | R² | R³ | n | Ar |
|---|---|---|---|---|
| H | CH₃ | H | 2 | 2,6-Cl₂-4-OCF₃-C₆H₂ |
| H | C₂H₅ | H | 0 | 2,6-Cl₂-4-OCF₃-C₆H₂ |
| H | C₂H₅ | H | 1 | 2,6-Cl₂-4-OCF₃-C₆H₂ |
| H | C₂H₅ | H | 2 | 2,6-Cl₂-4-OCF₃-C₆H₂ |
| CH₃ | CH₃ | H | 0 | 2,6-Cl₂-4-OCF₃-C₆H₂ |
| CH₃ | CH₃ | H | 1 | 2,6-Cl₂-4-OCF₃-C₆H₂ |
| CH₃ | CH₃ | H | 2 | 2,6-Cl₂-4-OCF₃-C₆H₂ |
| H | CF₃ | H | 0 | 2,6-Cl₂-4-OCF₃-C₆H₂ |
| H | CF₃ | H | 1 | 2,6-Cl₂-4-OCF₃-C₆H₂ |

-continued

| R¹ | R² | R³ | n | Ar |
|---|---|---|---|---|
| H | CF₃ | H | 2 | 2,6-Cl₂-4-OCF₃-C₆H₂ |
| H | CCl₂F | CH₃ | 0 | 2,6-Cl₂-4-OCF₃-C₆H₂ |
| H | CClF₂ | H | 0 | 2,6-Cl₂-4-OCF₃-C₆H₂ |
| H | CClF₂ | H | 1 | 2,6-Cl₂-4-OCF₃-C₆H₂ |
| H | CClF₂ | CH₃ | 1 | 2,6-Cl₂-4-OCF₃-C₆H₂ |
| H | CClF₂ | H | 2 | 2,6-Cl₂-4-OCF₃-C₆H₂ |
| H | CF₃ | —CH₂CH₂—OH | 0 | 2,6-Cl₂-4-CF₃-C₆H₂ |
| H | CF₃ | —CH₂CH₂—OH | 1 | 2,6-Cl₂-4-CF₃-C₆H₂ |
| H | CF₃ | CH₃ | 0 | 2,6-Cl₂-4-CF₃-C₆H₂ |

-continued

| R¹ | R² | R³ | n | Ar |
|---|---|---|---|---|
| H | CCl₂F | —CH₂CH₂—OH | 1 | 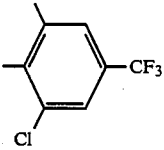 |
| H | CF₃ | H | 0 | 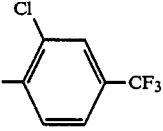 |
| H | CF₃ | H | 1 | 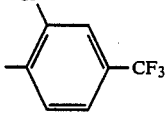 |
| H | CF₃ | H | 2 | 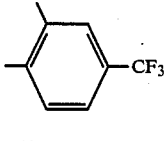 |
| CH₃ | CF₃ | H | 0 | 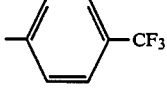 |
| CH₃ | CF₃ | H | 1 | 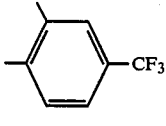 |
| CH₃ | CF₃ | H | 2 | 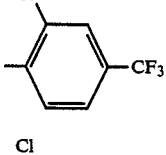 |
| CH₃ | CClF₂ | H | 0 | 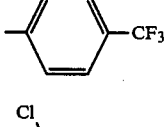 |
| H | CClF₂ | H | 0 | 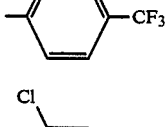 |
| CF₃ | CCl₂F | H | 0 | 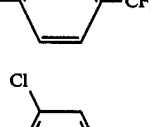 |
| C₂H₅ | CF₃ | H | 0 |  |

-continued

| R¹ | R² | R³ | n | Ar |
|---|---|---|---|---|
| H | C₂H₅ | H | 0 | 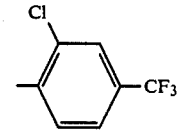 |
| H | C₂H₅ | H | 1 | 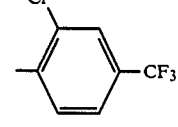 |
| H | C₂H₅ | H | 2 | 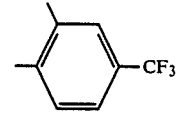 |
| H | C₂H₅ | CH₃ | 0 | |

The 5-aminopyrazole derivatives of the formula (I) to be used according to the invention are known in some cases (compare, for example, Pharmaco. Ed. Sci. 26, 276–293 [1971] or Mycopathologica 74, 7–14 [1981] compare also C.A. 96; 196411j and C.A. 95; 36257q), and some of them are the subject of a previous Patent Application which has been filed by the Applicant Company and has not yet been published (compare German Pat. No. 3,402,308 of 24.1.1984) and can be obtained by a process analogous to the preparation processes described therein. Compounds of the formula (I) which are not yet known from the abovementioned literature are those in which R¹ in each case represents hydrogen and
(a) R² represents optionally substituted benzyl (R³, n and Ar having the abovementioned meaning), or
(b) Ar represents unsubstituted or monosubstituted phenyl (R², R³ and n having the abovementioned meaning) [with the exception of the compound: 5-amino-4-(4-chlorophenylsulphonyl)-1-phenyl-pyrazole; compare: Khim. Geterotsikl. Soedin. 1978, 969–971 and C.A. 89; 179950x]
(c) Ar represents polysubstituted phenyl, but the 2- and 4-position may not be simultaneously substituted (and R², R³ and n have the above-mentioned meaning).

These compounds can be prepared by a process analogous to the known processes or to those described here (for example by reaction of substituted arylhydrazines with acrylonitrile derivatives with cyclization to give 1-aryl-5-amino-pyrazoles and, if appropriate, subsequent further derivatization).

5-Aminopyrazoles which are also not yet known are those of the formula (Ia)

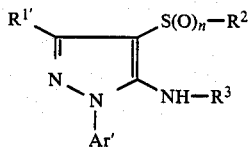

(Ia)

in which
R$^{1'}$ represents alkyl or halogenoalkyl,
Ar' represents substituted phenyl, or represents optionally substituted pyridyl and
R$^2$, R$^3$ and n have the abovementioned meanings,
but R$^2$ only represents s-butyl if, at the same time, R$^1$ does not represent methyl, R$^3$ does not represent hydrogen, n does not represent O and Ar does not represent phenyl which is monosubstituted or disubstituted by chlorine.

5-Amino-pyrazoles which are likewise not yet known are those of the formula (Ib)

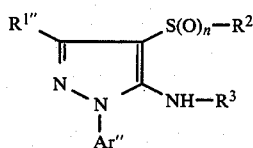

(Ib)

in which
R$^{1''}$ represents hydrogen,
Ar'' represents optionally substituted 2-pyridyl, 3-pyridyl or 4-pyridyl and
R$^2$, R$^3$ and n have the abovementioned meanings.

The aminopyrazoles of the formula (Ia) which are not yet known are obtained, for example, by a process in which (a) (α) 4-thiocyanato-5-aminopyrazoles of the general formula (IIa)

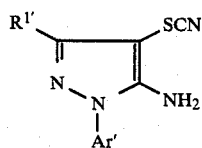

(IIa)

in which
R$^{1'}$ and Ar' have the abovementioned meaning, or
(a) (β) bis-(pyrazolyl) disulphides of the formula (IIIa)

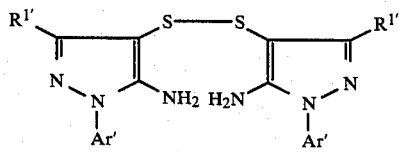

(IIIa)

in which
R$^{1'}$ and Ar' have the abovementioned meaning,
are reacted with halides of the formula (IV)

R$^2$—Hal (IV)

in which
R$^2$ has the abovementioned meaning and
Hal represents halogen, if appropriate in the presence of a diluent and in the presence of a suitable reducing agent and in the presence of a base, or in which (b) 4-unsubstituted 5-amino-pyrazoles of the formula (Va)

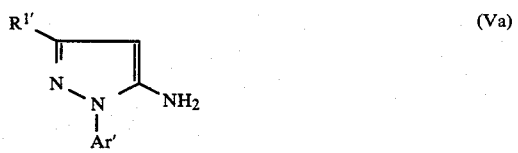

(Va)

in which
R$^{1'}$ and Ar' have the abovementioned meanings,
are reacted with sulphenyl halides of the formula (VI)

R$^2$—S—Hal' (VI)

in which
R$^2$ has the abovementioned meaning and
Hal' represents halogen, if appropriate in the presence of a diluent and if appropriate in the presence of an acid-binding agent, or in which (c) the 4-substituted 5-amino-pyrazoles obtainable by process (a-α), (a-β) or (b), of the formula (Ic)

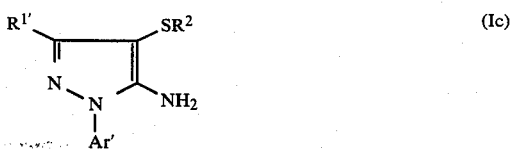

(Ic)

in which
R$^{1'}$, R$^2$ and Ar have the abovementioned meaning, are alkylated or acylated on the nitrogen of the amino group in the 5-position of the pyrazole ring in the generally customary manner with acylating agents or alkylating agents of the formula (VII)

R$^6$—A (VII)

in which
R$^6$ represents alkyl or a radical

wherein
X and R$^4$ have the abovementioned meaning and
A represents an electron-withdrawing leaving group,
or with iso(thio)cyanates of the formula (VIII)

R$^7$—N=C=X (VIII)

in which
R$^7$ represents alkyl or an optionally substituted aryl and
X has the abovementioned meaning, if appropriate in the presence of a diluent and if appropriate in the presence of an acid-binding agent, or in which (d) the 5-aminopyrazoles obtainable by process (a-α), (a-β), (b) or (c), of the formula (Id)

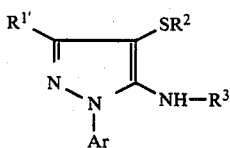 (Id)

in which
R$^{1'}$, R$^2$, R$^3$ and Ar' have the abovementioned meaning,
are oxidised on the sulphur of the sulphenyls group in the 4-position of the pyrazole ring with oxidising agents of the formula (IX)

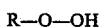  (IX)

in which
R represents hydrogen, or represents in each case optionally substituted alkanoyl or aroyl, if appropriate in the presence of a diluent, if appropriate in the presence of a catalyst and if appropriate in the presence of an acid-binding agent.

The 5-aminopyrazoles of the formula (Ib) which are not yet known are obtained analogously, for example by a process in which (e-α) 4-thiocyanato-5-aminopyrazoles of the general formula (IIb)

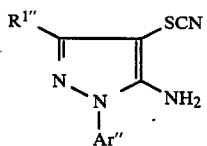 (IIb)

in which
R$^{1''}$ and Ar'' have the abovementioned meaning, or
(e-β) bis-(pyrazolyl) disulphides of the formula (IIIb)

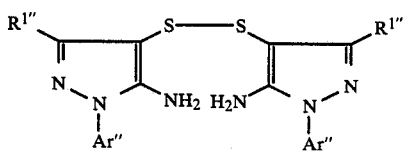 (IIIb)

in which
R$^{1''}$ and Ar'' have the abovementioned meaning,
are reacted with halides of the formula (IV)

 (IV)

in which
R$^2$ has the abovementioned meaning and
Hal represents halogen,
if appropriate in the presence of a diluent and in the presence of a suitable reducing agent and in the presence of a base, or in which (f) 4-unsubstituted 5-amino-pyrazoles of the formula (Vb)

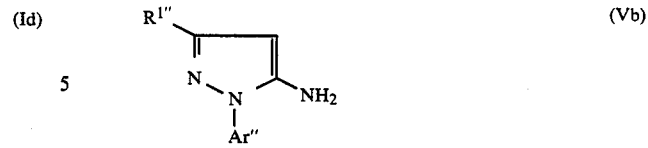 (Vb)

in which
R$^{1''}$ and Ar'' have the abovementioned meaning,
are reacted with sulphenyl halides of the formula (VI)

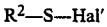 (VI)

in which
R$^2$ has the abovementioned meaning and
Hal' represents halogen,
if appropriate in the presence of a diluent and if appropriate in the presence of an acid-binding agent, or in which (g) the 4-substituted 5-amino-pyrazoles obtainable by process (e-α), (e-β) or (f), of the formula (Ie)

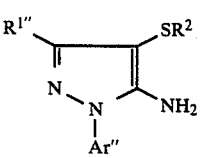 (Ie)

in which
R$^{1''}$, R$^2$ and Ar'' have the abovementioned meaning,
are alkylated or acylated on the nitrogen of the amino group in the 5-position of the pyrazole ring in the generally customary manner with acylating agents or alkylating agents of the formula (VII)

 (VII)

in which
R$^6$ represents alkyl or a radical

wherein
X and R$^4$ have the abovementioned meaning and
A represents an electron-withdrawing leaving group, or with iso(thio)cyanates of the formula (VIII)

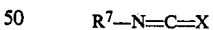 (VIII)

in which
R$^7$ represents alkyl or optionally substituted aryl and
X has the abovementioned meaning,
if appropriate in the presence of a diluent and if appropriate in the presence of an acid-binding agent, or in which (h) the 5-aminopyrazoles obtainable by process (e-α), (e-β), (f) or (g), of the formula (If)

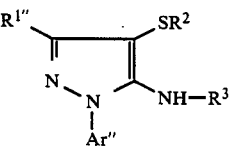 (If)

in which

R¹″, R², R³ and Ar″ have the abovementioned meaning, are oxidised at the sulphur of the sulphenyl group in the 4-position of the pyrazole ring with oxidising agents of the formula (IX)

R—O—OH        (IX)

in which

R represents hydrogen, or represents in each case optionally substituted alkanoyl or aroyl, if appropriate in the presence of a diluent, if appropriate in the presence of a catalyst and if appropriate in the presence of an acid-binding agent.

If, for example, 5-amino-1-(2,4-dichlorophenyl)-3-methyl-pyrazol-4-yl thiocyanate and methyl iodide are used as starting substances and sodium borohydride is used as the reducing agent, the course of the reaction in preparation process (a-α) can be represented by the following equation:

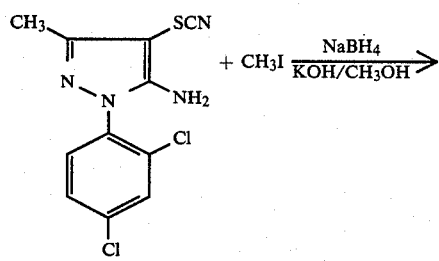

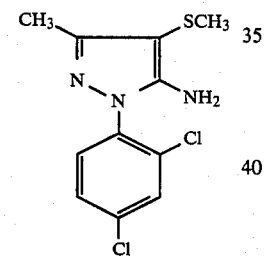

If, for example, S,S′-bis-[5-amino-1-(2,6-dichloro-4-trifluoromethylphenyl)-3-methylpyrazol-4-yl]disulphide and 4-chlorobenzyl bromide are used as starting substances and sodium dithionite is used as the reducing agent, the course of the reaction in preparation process (a-β) can be represented by the following equation:

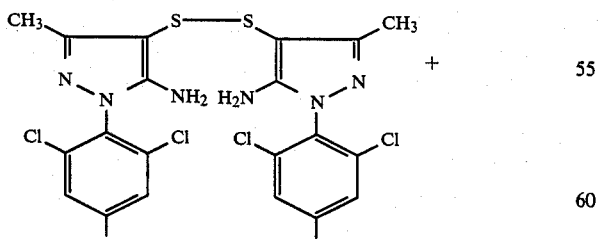

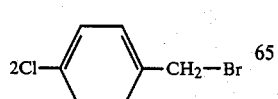

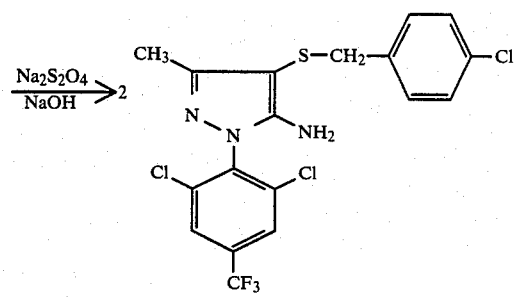

If, for example, 5-amino-3-methyl-1-(2,4,6-trichlorophenyl)-pyrazole and dichlorofluoromethanesulphenyl chloride are used as starting substances, the course of the reaction in preparation process (b) can be represented by the following equation:

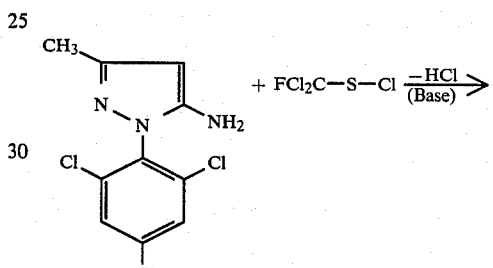

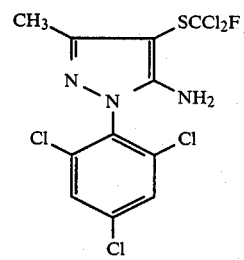

If, for example, 5-amino-3-methyl-4-trifluoromethylsulphenyl-1-(3,5-dichloropyrid-2-yl)-pyrazole and propionyl chloride are used as starting substances, the course of the reaction in preparation process (c) can be represented by the following equation:

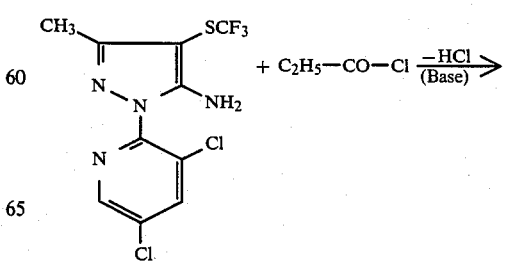

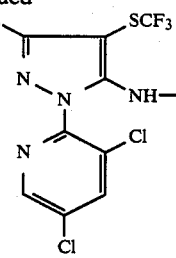

If, for example, 4-methyl-3-methylthio-1-(2,6-dichloro-4-trifluoromethylphenyl)-5-propionamido-pyrazole and m-chloroperbenzoic acid are used as starting substances, the course of the reaction in preparation process (d) can be represented by the following equation:

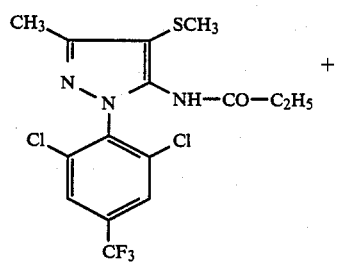

+

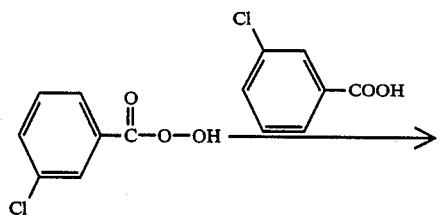

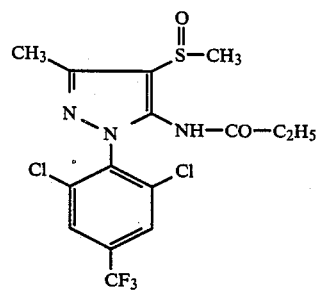

If, for example, (5-amino-1-pyrid-2-yl)-pyrazol-4-yl thiocyanate and methyl iodide are used as starting substances and sodium borohydride is used as the reducing agent, the course of the reaction in preparation process (e-α) can be represented by the following equation:

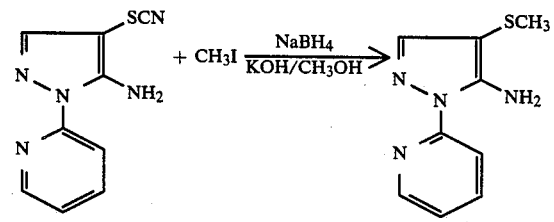

If, for example, S,S'-bis-[5-amino-1-(3-chloro-5-trifluoromethylthio-pyrid-2-yl)-pyrazol-4-yl]disulphide and 4-fluorobenzyl bromide are used as starting substances and sodium dithionite is used as the reducing agent, the course of the reaction in preparation process (e-β) can be represented by the following equation:

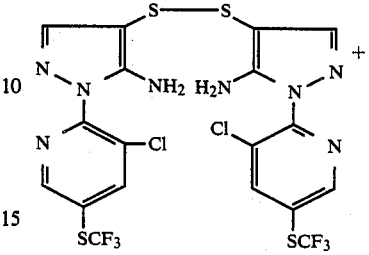

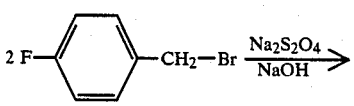

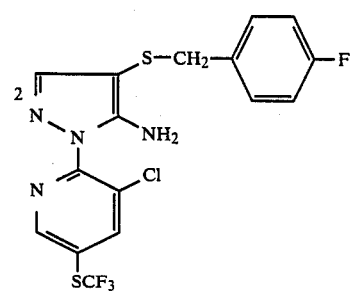

If, for example, 5-amino-1-(5-chloro-pyrid-2-yl)pyrazole and trichloromethylsulphenyl chloride are used as starting substances, the course of the reaction in preparation process (f) can be represented by the following equation:

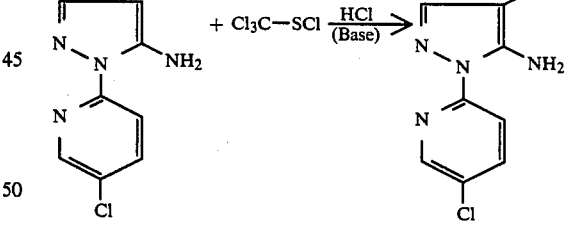

If, for example, 5-amino-4-ethylthio-1-pyrid-4-yl-pyrazole and propionyl chloride are used as starting substances, the course of the reaction in preparation process (g) can be represented by the following equation:

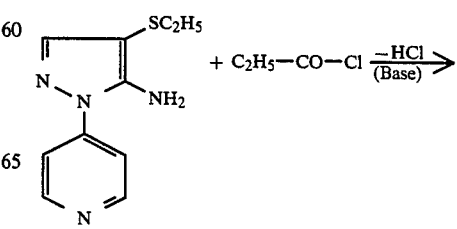

-continued

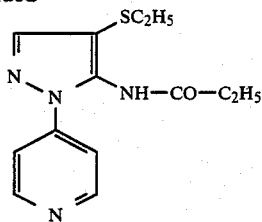

If, for example, 4-ethylthio-1-(3,5-dichloropyrid-4-yl)-5-propionamido-pyrazole and hydrogen peroxide are used as starting substances, the course of the reaction in preparation process (h) can be represented by the following equation:

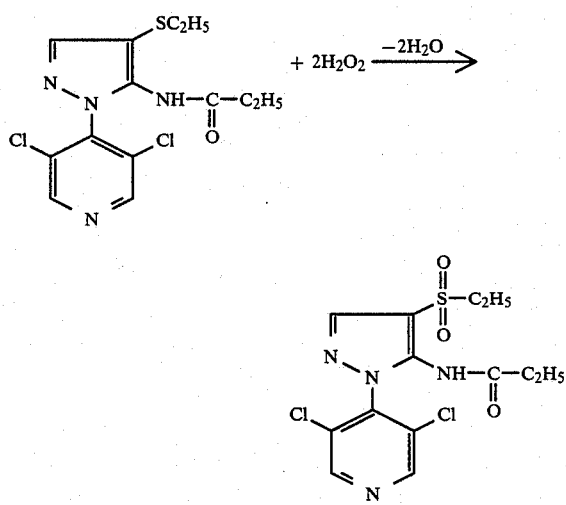

Formulae (IIa) and (IIb) provide general definitions of the 4-thiocyanato-5-amino-pyrazoles required as starting substances for carrying out preparation processes (a-α) and (e-α). In formula (IIa), $R^{1'}$ preferably represents in each case straight-chain or branched alkyl or halogenoalkyl with 1 to 4 carbon atoms and, where appropriate, 1 to 9 halogen atoms for methyl, ethyl, n- or i-propyl or trifluoromethyl, Ar' preferably represents phenyl which is monosubstituted or polysubstituted by identical or different substituents, or represents 2-pyridyl, 3-pyridyl or 4-pyridyl, optionally monosubstituted or polysubstituted by identical or different substituents, possible substituents in each case being: cyano, nitro, halogen, in each case straight-chain or branched alkyl, alkoxy or alkoxycarbonyl with in each case up to 4 carbon atoms, in each case straight-chain or branched halogenoalkyl or halogenoalkoxy with in each case up to 4 carbon atoms and up to 9 identical or different halogen atoms and a radical —S(O)$_m$—R$^5$ wherein R$^5$ represents amino, or represents in each case straight-chain or branched alkyl, alkylamino, dialkylamino or halogenoalkyl with in each case up to 4 carbon atoms in the individual alkyl parts and, in the case of halogenoalkyl, with up to 9 identical or different halogen atoms and m represents the number 0, 1 or 2.

In formula (IIb), $R^{1''}$ preferably represents hydrogen and Ar'' preferably represents 2-pyridyl, 3-pyridyl or 4-pyridyl, optionally monosubstituted or polysubstituted by identical or different substituents, possible substituents being those mentioned for Ar'.

The 4-thiocyanato-5-aminopyrazoles of the formulae (IIa) and (IIb) are known in some cases (compare, for example, Farmaco Ed. Sci. 38, 274–282 [1983]). They are obtained, for example, when 4-unsubstituted 5-aminopyrazoles of the formula (V)

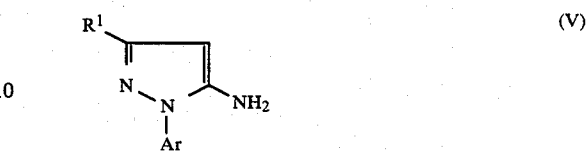

in which

R$^1$ represents hydrogen, alkyl or halogenoalkyl and
Ar represents substituted phenyl or in each case optionally substituted 2-pyridyl, 3-pyridyl or 4-pyridyl, are reacted with ammonium thiocyanate in the presence of bromine and acetic acid at temperatures between −20° C. and +20° C.

Formulae (IIIa) and (IIIb) provide general definitions of the bis-(pyrazolyl)disulphides required as starting substances for carrying out preparation process (a-β) and (e-β). In formulae (IIIa) and (IIIb), the radicals $R^{1'}$ and $R^{1''}$ and Ar' and Ar'' preferably represent those radicals which have already been mentioned as preferred for these substituents in connection with the description of the precursors of the formulae (IIa) and (IIb).

The bis-(pyrazolyl)disulphides of the formulae (IIIa) and (IIIb) are not yet known. They are obtained when the 4-thiocyanato-5-amino-pyrazoles of the formulae (IIa) and (IIb) described above are reacted with aqueous hydrochloric acid, if appropriate in the presence of a diluent, such as, for example, ethanol, at temperatures between 20° C. and 120° C.

Formula (IV) provides a general definition of the halides furthermore required as starting substances for carrying out preparation processes (a-α), (a-β), (e-α) and (e-β). In this formula (IV), R$^2$ preferably represents those substituents which have already been mentioned as preferred for this radical in connection with the description of the 5-aminopyrazole derivatives of the formula (I) which can be used according to the invention. Hal preferably represents chlorine, bromine or iodine. The halides of the formula (IV) are generally known compounds of organic chemistry.

Formulae (Va) and (Vb) provide general definitions of the 4-unsubstituted 5-aminopyrazoles required as starting substances for carrying out preparation processes (b) and (f) and for the synthesis of the precursors of the formulae (IIa) and (IIb). In formulae (Va) and (Vb), the radicals $R^{1'}$ and $R^{1''}$ and Ar' and Ar'' preferably represent those radicals which have already been mentioned as preferred for these substituents in connection with the description of the precursors of the formulae (IIa) and (IIb).

The 4-unsubstituted 5-aminopyrazoles of the formulae (Va) and (Vb) are known in some cases (compare, for example, J. Org. Chem. 36, 2972–2974 [1971] or J. Heterocyclic Chemistry 7, 345–349 [1970]; C.A. 62: 13137c).

They are obtained, for example, by a process in which arylhydrazines of the formula (X)

Ar'''—NH—NH$_2$     (X)

in which
Ar''' represents substituted phenyl, or represents in each case optionally substituted 2-pyridyl, 3-pyridyl or 4-pyridyl,
are either reacted initially in a first stage with acrylonitrile derivatives of the formula (XI)

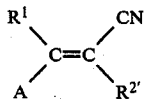 (XI)

in which
R$^1$ represents hydrogen, alkyl or halogenoalkyl,
R$^{2'}$ represents hydrogen or alkoxycarbonyl and
A represents halogen, hydroxyl, alkoxy, amino or dialkylamino,
if appropriate in the presence of a diluent, such as, for example, ethanol or glacial acetic acid, and if appropriate in the presence of a reaction auxiliary, such as, for example, sodium acetate, at temperatures between −20° C. and +20+ C. to give the arylhydrazine derivatives of the formula (XII)

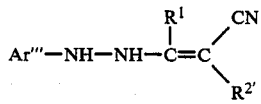 (XII)

in which
Ar''', R$^1$ and R$^{2'}$ have the abovementioned meaning, and these are cyclised in a 2nd stage, if appropriate in the presence of a diluent, such as, for example, ethylene glycol monoethyl ether, at temperatures between +50° C. and +150° C. or are cyclised directly in one reaction step without isolation of the intermediate stage of the formula (XII), if appropriate in the presence of a diluent, such as, for example, ethylene glycol monoethyl ether, at temperatures between +50° C. and +150° C., directly to give the 5-aminopyrazoles of the formula (XIII)

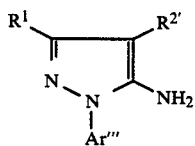 (XIII)

in which
R$^1$, R$^{2'}$ and Ar''' have the abovementioned meaning, and, in the case where R$^{2'}$ represents alkoxycarbonyl, the compounds of the formula (XIII) are hydrolysed and decarboxylated in the generally customary manner, if appropriate in the presence of a diluent, such as, for example, ethanol or isopropanol, and if appropriate in the presence of a catalyst, such as, for example, hydrobromic acid, at temperatures between 50° C. and 150° C.

The arylhydrazines of the formula (X) are known (compare, for example, U.S. Pat. No. 4,127,575; U.S. Pat. No. 3,609,158; DE-OS (German Published Specification) No. 2,558,399; and J. Chem. Soc. C, 1971, 167–174), or they can be prepared by processes which are known in principle in a simple analogous manner (compare, for example, Houben-Weyl "Methoden der organischen Chemie" ("Methods of Organic Chemistry") Volume X, 2 page 203, Thieme Verlag Stuttgart 1967).

The acrylonitrile derivatives of the formula (XI) are generally known compounds of organic chemistry.

Formula (VI) provides a general definition of the sulphenyl halides furthermore required as starting substances for carrying out preparation processes (b) and (f). In this formulae (VI), R$^2$ preferably represents those substituents which have already been mentioned as preferred for this radical in connection with the description of the substances of the formula (I) which can be used according to the invention. Hal' preferably represents fluorine, chlorine, bromine or iodine.

The sulphenyl halides of the formula (VI) are generally known compounds of organic chemistry.

Formula (Ic) and (Ie) provide general definitions of the 4-substituted 5-aminopyrazoles required as starting substances for carrying out preparation processes (c) and (g). In these formulae (Ic) and (Ie), R$^{1'}$ and R$^{1''}$ and Ar' and Ar'' preferably represent those radicals which have already been mentioned as preferred for these substituents in connection with the description of the precursors of the formulae (IIa) and (IIb). R$^2$ preferably represents those radicals which have already been mentioned as preferred for this radical in connection with the description of the substances of the formula (I) which can be used according to the invention.

The 4-substituted 5-aminopyrazoles of the formulae (Ic) and (Ie) are compounds according to the invention and can be obtained with the aid of preparation processes (a-α), (a-β) or (b) or (e-α), (e-β) or (f).

Formula (VII) provides a general definition of the acylating or alkylating agents furthermore required as starting substances for carrying out preparation processes (c) and (g). In this formula (VII), R$^6$ preferably represents straight-chain or branched alkyl with up to 4 carbon atoms, or represents a radical

wherein
X and R$^4$ preferably represent those radicals which have already been mentioned for these radicals in the description of the substances of the formula (I) which can be used according to the invention.

A preferably represents chlorine, bromine, iodine, p-toluenesulphonyloxy, alkoxysulphonyloxy or acyloxy. The alkylating and acylating agents of the formula (VII) are generally known compounds of organic chemistry.

Formula (VIII) provides a general definition of the iso(thio)cyanates which can alternatively be used as starting substances for carrying out preparation processes (c) and (g). In this formula, X preferably represents oxygen or sulphur and R$^7$ preferably represents straight-chain or branched alkyl with up to 4 carbon atoms, or represents phenyl which is optionally mono-, di- or trisubstituted by identical or different substituents, possible substituents being: halogen and in each case straight-chain or branched alkyl, alkoxy or halogenoalkyl with in each case up to 4 carbon atoms and, in the case of the halogenoalkyl, with up to 9 identical or different halogen atoms.

R$^7$ represents, in particular, methyl, ethyl, or phenyl which is optionally mono-, di- or trisubstituted by identical or different substituents from the group comprising fluorine, chlorine, methyl, methoxy or trifluoromethyl.

The iso(thio)cyanates of the formula (VIII) are likewise generally known compounds of organic chemistry.

Formulae (Id) and (If) provide general definitions of the 5-aminopyrazoles required as starting substances for carrying out preparation processes (d) and (h). In these formulae (Id) and (If), $R^{1'}$ and $R^{1''}$ and $Ar'$ and $Ar''$ preferably represent those radicals which have already been mentioned as preferred for these substituents in connection with the description of the precursors of the formulae (IIa) and (IIb). $R^2$ and $R^3$ preferably represent those radicals which have already been mentioned as preferred for these radicals in connection with the description of the substances of the formula (I) which can be used according to the invention.

The 5-aminopyrazoles of the formulae (Id) and (If) are compounds according to the invention and can be obtained with the aid of preparation processes (a-$\alpha$), (a-$\beta$), (b) or (c) or (e-$\alpha$), (e-$\beta$), (f) or (g).

Formula (IX) provides a general definition of the oxidising agents furthermore required as starting substances for carrying out preparation processes (d) and (h). In this formula (IX), R preferably represents hydrogen, or represents acetyl, or represents propionyl, or represents trifluoroacetyl, or represents optionally substituted benzoyl, such as, for example, 3-chlorobenzoyl or 4-nitrobenzoyl. The oxidising agents of the formula (IX) are generally known compounds of organic chemistry.

Possible diluents for carrying out preparation processes (a-$\alpha$) and (a-$\beta$) and (e-$\alpha$) and (e-$\beta$) are inert organic solvents.

These include, in particular, aliphatic or aromatic optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, or alcohols, such as methanol, ethanol or propanol.

The alcohol corresponding in the alkyl radical to the halide of the formula (IV) is particularly advantageously used as the diluent, that is to say, for example, if methyl iodide is used as the halide of the formula (IV), methanol is particularly preferably suitable as the diluent.

Reducing agents which are used for carrying out preparation processes (a-$\alpha$) and (e-$\alpha$) are preferably complex hydrides, such as lithium aluminium hydride, lithium borohydride or sodium borohydride. Sodium borohydride is particularly suitable.

Possible reducing agents for carrying out preparation processes (a-$\beta$) and (e-$\beta$) are all the reducing agents which can usually be employed for disulphide cleavages. Dithionites, such as, for example, sodium dithionite, are particularly preferably used.

Preparation processes (a-$\alpha$), (a-$\beta$), (e-$\alpha$) and (e-$\beta$) are carried out in the presence of a suitable base. Alkali metal hydroxides or carbonates, such as, for example, sodium or potassium hydroxide or sodium or potassium carbonate, are preferably used.

The reaction temperatures can be varied within a substantial range in carrying out preparation processes (a-$\alpha$), (a-$\beta$), (e-$\alpha$) and (e-$\beta$). The reaction is in general carried out at temperatures between 0° C. and +120° C., preferably at temperatures between +20° C. and +90° C.

For carrying out preparation processes (a-$\alpha$) and (e-$\alpha$), in general 1.0 to 5.0 moles, preferably 1.8 to 2.5 moles, of halide of the formula (IV) and 1.0 to 5.0 moles, preferably 1.8 to 2.0 moles, of reducing agent and 1.0 to 5.0 moles, preferably 1.5 to 3.0 moles, of base are employed per mole of 4-thiocyanato-5-aminopyrazole of the formula (IIa) or (IIb). In this reaction, the 4-thiocyanato-5-aminopyrazole of the formula (IIa) or (IIb) is reacted with the reducing agent in the diluent in question, using a protective gas atmosphere of nitrogen, and, when the reaction has ended, the base and the halide of the formula (IV) are added. Working up and isolation of the reaction products of the formula (Ia) or (Ib) are carried out by customary processes.

For carrying out preparation processes (a-$\beta$) and (e-$\beta$), in general 1.0 to 5.0 moles, preferably 1.8 to 2.5 moles, of halide of the formula (IV) and 1.0 to 5.0 moles, preferably 1.8 to 2.0 moles, of reducing agent and 1.0 to 5.0 moles, preferably 1.5 to 3.0 moles, of base are employed per mole of bis-(pyrazolyl)disulphide of the formula (IIIa) or (IIIb). In this reaction, the bis-(pyrazolyl)disulphide of the formula (IIIa) or (IIIb) is first reacted with the reducing agent in the diluent in question in the presence of the base at the corresponding reaction temperature, the halide of the formula (IV) is added after a few hours and the mixture is warmed at the required reaction temperature for a further hour. Working up and isolation of the reaction products of the formulae (Ia) and (Ib) are carried out by customary processes.

Possible diluents for carrying out preparation processes (b) and (f) are inert organic solvents.

These include, in particular, aliphatic or aromatic optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, diethylacetamide, N-methylformanilide, N-methylpyrrolidone or hexamethylphosphoric acid triamide, esters, such as ethyl acetate, or sulphoxides, such as dimethylsulphoxide.

If appropriate, preparation processes (b) and (f) are carried out in the presence of an acid-binding agent. Possible acid-binding agents are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazobicyclononene (DBN) or diazabicycloundecene (DBU).

The reaction temperatures can be varied within a substantial range in carrying out preparation processes (b) and (f). The reaction is in general carried out at temperatures between −20° C. and +120° C., preferably at temperatures between 0° C. and +50° C.

For carrying out preparation processes (b) and (f), in general 1.0 to 2.5 moles, preferably 1.0 to 1.5 moles, of sulphenyl halide and 1.0 to 2.5 moles, preferably 1.0 to 1.5 moles, of acid-binding agent are employed per mole of 4-unsubstituted 5-amino-pyrazole of the formula (Va) or (Vb). The reaction is carried out and the reaction products of the formulae (Ia) and (Ib) are worked up and isolated by generally customary processes.

Possible diluents for carrying out preparation processes (c) and (g) are likewise inert organic solvents. The organic solvents mentioned in the description of preparation processes (b) and (f) are preferably used as diluents.

If appropriate, preparation processes (c) and (g) are carried out in the presence of an acid-binding agent. Possible acid-binding agents are, in particular, the organic and inorganic bases mentioned in the description of preparation processes (b) and (f).

The reaction temperatures can be varied within a substantial range in carrying out preparation processes (c) and (g). The reaction is in general carried out at temperatures between $-20°$ C. and $+80°$ C., preferably at temperatures between $-10°$ C. and $+40°$ C.

For carrying out preparation processes (c) and (g), in general 1.0 to 10.0 moles, preferably 1.0 to 5.0 moles, of acylating or alkylating agent of the formula (VII) or iso(thio)cyanate of the formula (VIII) and, if appropriate, 1.0 to 5.0 moles of acid-binding agent are employed per mole of 4-substituted 5-amino-pyrazole of the formula (Ic) or (Ie). The reaction is carried out and the reaction products of the formulae (Ia) and (Ib) are worked up and isolated by generally known customary processes.

Possible diluents for carrying out preparation processes (d) and (h) are likewise inert organic solvents.

Solvent which are preferably used are hydrocarbons, such as benzine, benzene, toluene, hexene or petroleum ether; chlorinated hydrocarbons, such as methylene chloride, 1,2-dichloroethene, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide.

If appropriate, preparation processes (d) and (h) can be carried out in the presence of an acid-binding agent. Possible acid-binding agents are all the organic and inorganic acid-binding agents which can usually be employed. Acid-binding agents which are preferably used are alkaline earth metal or alkali metal hydroxides, acetates or carbonates, such as, for example, calcium hydroxide, sodium hydroxide, sodium acetate or sodium carbonate.

If appropriate, preparation processes (d) and (h) can be carried out in the presence of a suitable catalyst. Possible catalysts are all the customary catalysts which are usually for such sulphur oxidations. Ammonium molybdate may be mentioned as an example in this connection.

The reaction temperatures can be varied within a substantial range in carrying out preparation processes (d) and (h). The reaction is in general carried out at temperatures between $-20°$ C. and $+70°$ C., preferably at temperatures between $0°$ C. and $+50°$ C.

For carrying out preparation processes (d) and (h), in general 0.8 to 1.2 moles, preferably equimolar amounts, of oxidising agent of the formula (IX), if the oxidation of the sulphur is to be interrupted at the sulphoxide stage, are employed per mole of 5-aminopyrazole of the formula (Id) or (If). For oxidation to the sulphone, in general 1.8 to 3.0 moles, preferably twice the molar amounts, of oxidising agent of the formula (IX) are employed per mole of 5-aminopyrazole of the formula (Id) or (If). The reaction is carried out and the end products of the formula (Ia) or (Ib) are worked up and isolated by customary methods.

The active compounds are well tolerated by plants, have a favourable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi,* Empoasca spp., Euscelis bilobatus, Nephotettix cinciceps, Lecanium corni, Saissetia oleae, Laodelphax striatellus, Nilaparvata lugens, Aonidiella aurantii, Aspidiotus hederae, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus,* Ceuthorrhyn-

*chus assimilis, Hypera postica,* Dermestes spp., Trogoderma spp., Anthrenus spp., Attagenus spp., Lyctus spp., *Meligethes aeneus,* Ptinus spp., *Niptus hololeucus Gibbium psylloides,* Tribolium spp., Tenebrio molitor, Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., and Tetranychus spp..

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

The active compounds of the formula (I) which can be used according to the invention are distinguished by a powerful insecticidal, acaricidal and nematicidal activity. They can be employed, in particular, against insects which damage plants, such as, for example, against caterpillars of the diamond back cabbage moth (*Plutella maculipennis*) or against the larvae of the mustard bettle (*Phaedon cochleariae*), and against mites which damage plants, such as, for example, against the common spider mite (*Tetranychus urticae*). In addition, they are outstandingly suitable for combating soil insects and nematodes and can be used, for example, for combating *Phorbia antiqua* grubs or nematodes of the genus *Meloidogyne incognita.* A remarkable root-systemic action, for example against *Phaedon cochleariae* larvae, is also to be emphasised. The nematicidal action of the active compounds which can be used according to the invention can also be confirmed in the in vitro test, for example against nematodes of the genus *Caenorhabditis elegans* which live as endoparasites.

The active compounds of the formula (I) which can be used according to the invention also have a powerful action against hygiene and pests of stored products and can be used, for example, for combating the oriental cockroach (*Blatta orientalis*) or for combating the common corn weevil (*Sitophilus granarius*). The active compounds according to the invention moreover can be employed with particularly good success for combating parasitic pests of warm-blooded animals (both ectoparasites and endoparasites), such as, for example, larvae of the goldfly (*Lucilia cuprina*), against cattle ticks (*Boophilus microplus*), against scab mites (*Psoroptes ovis*) against biting flies (*Stomoxys calcitrans*) or against the pasture cattle fly (*Musca autumnalis*).

The active compounds of the formula (I) which can be used according to the invention in addition also have a good fungicidal activity and can be employed for combating plant diseases, such as, for example, against the rice spot disease causative organism (*Pyricularia oryzae*) or against scab and Botrytis causative organisms.

When applied in appropriate amounts, the active compounds of the formula (I) which can be used according to the invention furthermore exhibit a herbicidal activity.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds which can be used according to the invention can be present in their commercially available formulations and in the use forms, prepared from these formulations, as a mixture with other active compounds, such as insecticides, baits, sterilising agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds which can be used according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, mites, ticks and the like in the field of livestock husbandry and animal breeding, it being possible to achieve better results, for example higher milk yields, a higher weight, a more attractive animal coat and a longer life and the like, by combating the pests.

The active compounds which can be used according to the invention are applied in these fields in a known manner, such as by external use in the form of, for example, dipping (dips), spraying (sprays), pouring on (pour-on and spot-on) and dusting.

The biological activity of the compounds according to the invention may be illustrated with the aid of the following examples.

PREPARATION EXAMPLES

Example 1

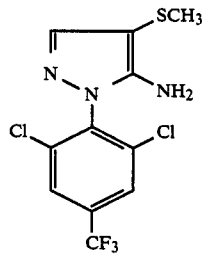

1.6 g (0.042 mole) of sodium borohydride are added in portions to 8 g (0.023 mole) of 5-amino-1-(2,6-dichloro-4-trifluoromethylphenyl)-pyrazol-4-yl thiocyanate in 100 ml of absolute methanol at room temperature in a nitrogen atmosphere. When the addition has ended, the mixture is stirred at room temperature for 45 minutes and a solution of 2.4 g (0.042 mole) of potassium hydroxide in 40 ml of absolute methanol is then added, and 6.0 g (0.042 mole) of methyl iodide are subsequently added dropwise. When the addition has ended, the mixture is stirred at room temperature for 30 minutes and concentrated in vacuo, the residue is taken up in water, the mixture is extracted several times with chloroform, the extract is dried over sodium sulphate, the solvent is removed in vacuo and the oil which remains is crystallized from petroleum ether.

6.1 g (78% of theory) of 5-amino-1-(2,6-dichloro-4-trifluoromethylphenyl)-4-methylthiopyrazole of melting point 106° C.–108° C. are obtained.

Preparation of the Starting Compound

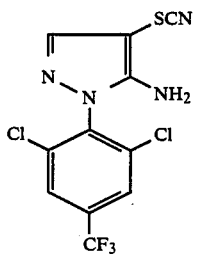

11.2 g (0.07 mole) of bromine in 70 ml of glacial acetic acid are added dropwise to 20.5 g (0.07 mole) of 5-amino-1-(2,6-dichloro-4-trifluoromethylphenyl)-pyrazole and 10.7 g (0.14 mole) of ammonium thiocyanate in 300 ml of glacial acetic acid at 10° C., with stirring, and, after the addition has ended, the mixture is stirred at +10° C. for a further 10 minutes. For working up, the mixture is poured onto ice and brought to pH 9 by addition of concentrated aqueous ammonia solution and the solid which has precipitated out is filtered off with suction and dried.

22.9 g (93% of theory) of 5-amino-1-(2,6-dichloro-4-trifluoromethylphenyl)-pyrazol-4-yl thiocyanate of melting point 137° C. are obtained.

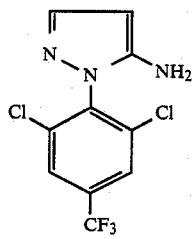

25 ml (27.6 g/0.3 mole) of 2-chloroacrylonitrile are added dropwise to 24.5 g (0.1 mole) of 2,6-dichloro-4-trifluoromethylphenyl-hydrazine with 20 mg of disodium ethylenediamine-tetraacetate (=Titriplex III) in 150 ml of methanol at the reflux temperature. When the addition has ended, the mixture is heated at the reflux temperature for a further 8 hours, 9 ml (0.16 mole) of 96% strength sulphuric acid are then added dropwise and the mixture is heated at the reflux temperature for a further 6 hours. 33.5 g (0.3 mole) of anhydrous sodium carbonate are added to the cooled reaction mixture. After 4 hours, the solvent is removed in vacuo, the residue is taken up in 500 ml of water and the mixture is stirred at room temperature for 10 hours. The precipitate which has separated out is filtered off, rinsed with water and dried in vacuo at 50° C.

28.5 g (96% of theory) of 5-amino-1-(2,6-dichloro-4-trifluoromethylphenyl)-pyrazole of melting point 103° C.–105° C. are obtained.

Example 2

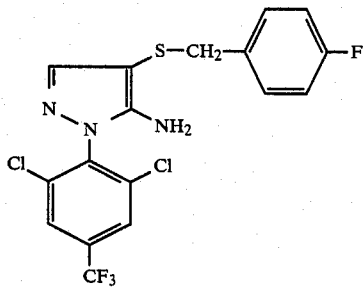

4.35 g (6.6 mmol) of S,S'-bis-[5-amino-1-(2,6-dichloro-4-trifluoromethylphenyl)-pyrazol-4-yl]disulphide, 0.5 g (13 mmol) of sodium hydroxide and 2.3 g (13 mmol) of sodium dithionite are heated under reflux in a mixture of 80 ml of ethanol and 80 ml of water for 2 hours. 2.45 g (13 mmol) of 4-fluorobenzyl bromide are then added and the mixture is heated under reflux for a further hour. For working up, it is concentrated to half the volume in vacuo, the concentrate is extracted several times with chloroform, the combined organic phases are dried over magnesium sulphate and the solvent is removed in vacuo. The oily residue crystallises on stirring with petroleum ether.

4.2 g (73% of theory) of 5-amino-1-(2,6-dichloro-4-trifluoromethylphenyl)-(4-fluorobenzylthio)-pyrazole of melting point 112° C.–113° C. are obtained.

Preparation of the starting compound

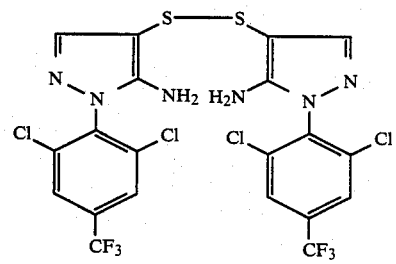

11.9 g (0.04 mole) of 5-amino-1-(2,6-dichloro-4-trifluoromethylphenyl)-pyrazol-4-yl thiocyanate are heated under reflux in a mixture of 300 ml of ethanol and 300 ml of water for 12 hours, after addition of 80 ml of 10 normal hydrochloric acid. For working up, the mixture is concentrated to half the volume in vacuo and the solid which has precipitated out is filtered off with suction.

10.4 g (80% of theory) of S,S'-bis-[5-amino-1-(2,6-dichloro-4-trifluoromethylphenyl)-pyrazol-4-yl]disulphide of melting point 148° C.–150° C. are obtained.

Example 3

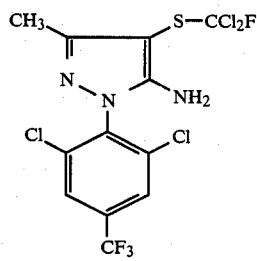

12.6 ml (0.12 mole) of dichlorofluoromethanesulphenyl chloride are added dropwise to 35.4 g (0.114 mole) of 5-amino-1-(2,6-dichloro-4-trifluoromethylphenyl)-3-methyl-pyrazole and 10 ml (0.125 mole) of anhydrous pyridine in 150 ml of methylene chloride at 0° C. to 5° C., with stirring. When the addition has ended, the mixture is stirred at room temperature for a further 30 minutes, 100 ml of methylene chloride are added, the mixture is washed in succession with dilute hydrochloric acid, water, sodium bicarbonate solution and aqueous sodium chloride solution and dried over magnesium sulphate and the solvent is removed in vacuo.

49.5 g (98% of theory) of 5-amino-1-(2,6-dichloro-4-trifluoromethylphenyl)-4-dichlorofluoromethylsulphenyl-3-methyl-pyrazole of melting point 131° C. are obtained.

Preparation of the starting compound

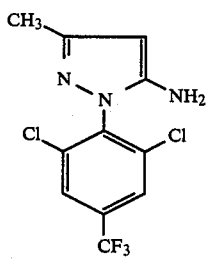

61.25 g (0.25 mole) of 2,6-dichloro-4-trifluoromethylphenyl hydrazine and 21 g (0.25 mole) of diacetonitrile are heated under relux in 500 ml of ethanol for 20 hours. 4 ml of concentrated sulphuric acid are added to the cooled reaction mixture and the mixture is heated at 60° C. for a further 4 hours. For working up, the mixture is evaporated in vacuo, the residue is taken up in chloroform and the mixture is rendered alkaline with 25 per cent strength aqueous ammonia solution. The organic phase is separated off and the aqueous phase is extracted with chloroform. The combined organic phases are dried over magnesium sulphate and freed from the solvent in vacuo.

62 g (80% of theory) of 5-amino-1-(2,6-dichloro-4-trifluoromethylphenyl)-3-methyl-pyrazole are obtained as a glass-like substance.

$^1$H-NMR (CDCl$_3$/TMS) δ=2.23; 3.50; 5.49; 7.68 ppm,

Example 4

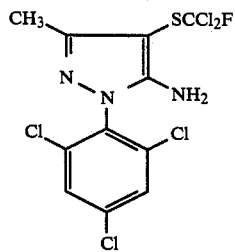

12.6 ml (0.12 mole) of dichlorofluoromethanesulphenyl chloride are added dropwise to 27.7 g (0.1 mole) of 5-amino-3-methyl-1-(2,4,6-trichlorophenyl)-pyrazole and 10 ml (0.125 mole) of anhydrous pyridine in 150 ml of methylene chloride at 0° C. to 5° C., with stirring, and the mixture is stirred for 30 minutes. For working up, 100 ml of methylene chloride are added, the mixture is washed in succession with dilute hydrochloric acid, water, sodium carbonate solution and sodium chloride solution and dried over magnesium sulphate and the solvent is removed in vacuo.

38.2 g (93% of theory) of 5-amino-4-dichlorofluoromethylsulphenyl-3-methyl-1-(2,4,6-trichlorophenyl)-pyrazole are obtained from melting point 125°-127° C.

Preparation of the starting compound

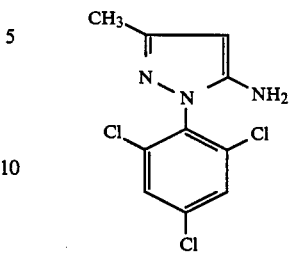

34.8 g (0.1 mole) of ethyl 5-amino-3-methyl-1-(2,4,6-trichlorophenyl)-pyrazol-4-ylcarboxylate are heated at 120° C. in a mixture of 250 ml of 48 percent strength hydrobromic acid and 25 ml of isopropanol for several hours. When the reaction has ended, 200 ml of water are added, the pH is brought to 7 to 8 with 10 percent strength sodium hydroxide solution and the solid which has precipitated out is filtered off with suction.

18 g (65% of theory) of 5-amino-3-methyl-1-(2,4,6-trichlorophenyl)-pyrazole of melting point 111° C.-113° C. are obtained.

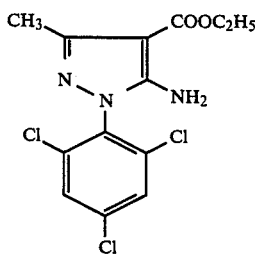

A solution of 21.2 g (0.1 mole) of 2,4,6-trichlorophenylhydrazine and 18.3 g (0.1 mole) of ethyl 2-cyano-3-ethoxy-2-butenoate in 250 ml of ethanol is heated under reflux for 14 hours and then concentrated in vacuo, the residue is taken up in methylene chloride and the mixture is washed with water, dried over magnesium sulphate and freed from the solvent in vacuo.

22 g (63% of theory) of ethyl 5-amino-3-methyl-1-(2,4,6-trichlorophenyl)-pyrazol-4-ylcarboxylate are obtained from melting point 150° C.

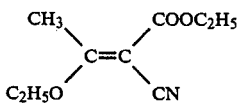

113 g (1 mole) of ethyl cyanoacetate, 162 g (1 mole) of triethylorthoacetate and 204 g (2 moles) of acetic anhydride are heated under reflux, during which ethyl acetate slowly distils off and the reaction temperature rises to 140° C. The residue is distilled under a water-pump vacuum.

57 g (32% of theory) of ethyl 2-cyano-3-ethoxy-2-butenoate of boiling point 150° C. under 24 mbar and of melting point 70° C. (recrystallization from isopropanol) are obtained.

Example 5

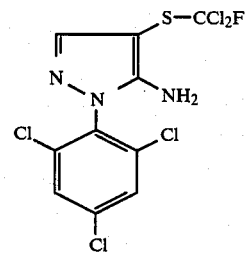

12.6 ml (0.12 mole) of dichlorofluoromethanesulphenyl chloride are added to 30 g (0.114 mole) of 5-amino-1-(2,4,6-trichlorophenyl)-pyrazole and 10 ml (0.125 mole) of anhydrous pyridine in 150 ml of methylene chloride at 0° C. to 5° C. and the mixture is stirred for 30 minutes. For working up, 100 ml of methylene chloride are added, the mixture is washed in succession with dilute hydrochloric acid, water, sodium bicarbonate solution and sodium chloride solution and dried over magnesium sulphate and the solvent is removed in vacuo.

44.5 g (98.7% of theory) of 5-amino-4-dichlorofluoromethanesulphenyl-1-(2,4,6-trichlorophenyl)-pyrazole of melting point 101° C. to 106° C. are obtained.

Example 6

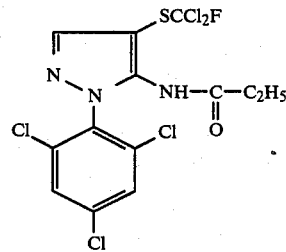

13.0 g (0.029 mole) of 5-amino-4-dichlorofluoromethylsulphenyl-1-(2,4,6-trichlorophenyl)-pyrazole are stirred with 50 ml of propionic anhydride and 1 ml of concentrated sulphuric acid at room temperature for 10 hours. The reaction mixture is then added dropwise to 100 ml of ice-cooled methanol, and the mixture is subsequently stirred for one hour and then evaporated to dryness. The residue is taken up in methylene chloride and the mixture is washed successively with water sodium bicarbonate solution and sodium chloride solution, dried over magnesium sulphate and freed from the solvent in vacuo.

8.9 g (68% of theory) of 4-dichlorofluoromethanesulphenyl-5-propionamido-1-(2,4,6-trichlorophenyl)-pyrazole of melting point 129° C. are obtained.

Example 7

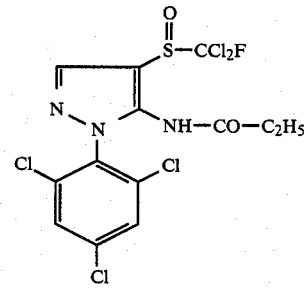

3 g (6.6 mmol) of 4-dichlorofluoromethanesulphenyl-5-propionamido-1-(2,4,6-trichlorophenyl)-pyrazole and 1.5 g (8.7 mmol) of m-chloroperbenzoic acid in 10 ml of methylene chloride are stirred at room temperature for 16 hours, the mixture is filtered and the filtrate is washed successively with sodium bicarbonate solution, sodium thiosulphate solution, again with sodium bicarbonate solution and then with sodium chloride solution, dried over magnesium sulphate and freed from the solvent in vacuo.

2.8 g (90.2% of theory) of 4-dichlorofluoromethylsulphinyl-5-propionamido-1-(2,4,6-trichlorophenyl)-pyrazole of melting point 146° C. are obtained.

The following 5-aminopyrazole derivatives of the general formula (I) are obtained in a corresponding manner and in accordance with the general preparation statements:

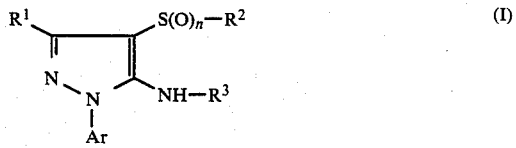

| Example No. | R¹ | R² | R³ | Ar | n | Physical properties |
|---|---|---|---|---|---|---|
| 8 | H | CCl₂F | CH₃—CH₂—CO | 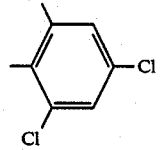 | 2 | Fp 139° C. |
| 9 | H | CF₃ | CH₃—CO | 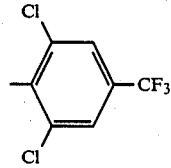 | 0 | Fp 131–138° C. |

-continued
| Example No. | R¹ | R² | R³ | Ar | n | Physical properties |
|---|---|---|---|---|---|---|
| 10 | H | CCl₂F | H | 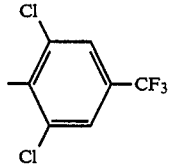 | 0 | Fp 99–105° C. |
| 11 | H | CCl₂F | H | 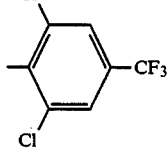 | 1 | Fp 55–62° C. |
| 12 | H | CCl₂F | H | 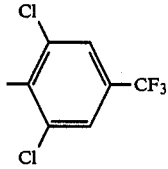 | 2 | Fp 135–138° C. |
| 13 | H | CCl₂F | H | 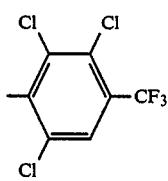 | 0 | Fp 60–65° C. |
| 14 | H | CCl₂F | H | 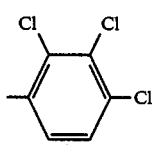 | 0 | Fp 55–62° C. |
| 15 | H | CCl₂F | H | 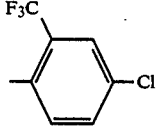 | 0 | NMR (3-H,Pyr.) 7.57 ppm (s,1H) (CDCl₃/TMS) |
| 16 | H | CCl₂F | H | 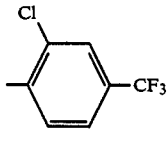 | 0 | Fp 81–87° C. |
| 17 | H | CCl₂F | H | 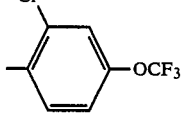 | 0 | Fp 77° C. |
| 18 | H | CCl₂F | H | 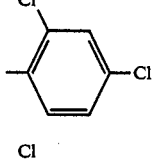 | 0 | NMR Oil (3-H,Pyr.) 7.61 ppm (s,1H) (CDCl₃/TMS) |
| 19 | H | CCl₂F | H | 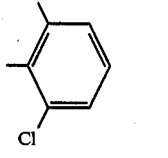 | 0 | Fp 112–121° C. |

-continued

| Example No. | R¹ | R² | R³ | Ar | n | Physical properties |
|---|---|---|---|---|---|---|
| 20 | H | CCl₂F | H | 2,3,5,6-tetrachloro-4-CF₃-phenyl | 0 | Fp 55–61° C. |
| 21 | H | CCl₂F | H | 5-CF₃-pyridin-2-yl | 0 | NMR Oil (3-H,Pyr), 7.58 ppm (s,1H) (CDCl₃/TMS) |
| 22 | H | CCl₂F | CH₃ | 2,6-dichloro-4-CF₃-phenyl | 0 | Fp 107–110° C. |
| 23 | H | CCl₂F | H | 2,6-dichloro-4-SO₂CF₃-phenyl | 0 | Fp 148–153° C. |
| 24 | H | CCl₃ | H | 2,6-dichloro-4-CF₃-phenyl | 0 | Fp 75–88° C. |
| 25 | H | CF₃ | H | 2,6-dichloro-4-CF₃-phenyl | 0 | Fp 86–94° C. |
| 26 | H | 3-CF₃-phenyl | H | 2,6-dichloro-4-CF₃-phenyl | 0 | NMR Oil (3-H,Pyr.) 7.64 ppm (s,1H) (CDCl₃/TMS) |
| 27 | H | CCl₂F | H | 2,6-dichloro-4-SCF₃-phenyl | 0 | Fp 104–107° C. |
| 28 | H | CCl₂F | H | 3,5-dichloro-pyridin-2-yl | 0 | NMR Oil (3-H,Pyr.) 7.64 ppm (s,1H) (CDCl₃/TMS) |

-continued
| Example No. | R¹ | R² | R³ | Ar | n | Physical properties |
|---|---|---|---|---|---|---|
| 29 | H | CCl₂F | H | 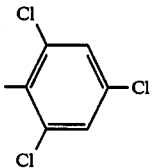 2,4,6-trichlorophenyl | 1 | Fp 69–75° C. |
| 30 | H | CCl₂F | H | 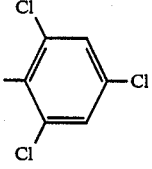 2,4,6-trichlorophenyl | 2 | Fp 63–69° C. |
| 31 | H | CCl₂F | H | 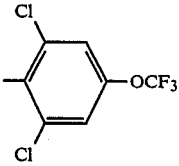 2,6-dichloro-4-OCF₃-phenyl | 0 | Fp 101–107° C. |
| 32 | H | CCl₂F | H | 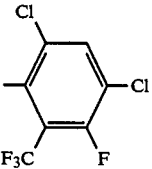 3,5-dichloro-2-fluoro-6-CF₃... | 0 | NMR: Oil (3-H,Pyr.) 7.67 ppm (s,1H) (CDCl₃/TMS) |
| 33 | H | CCl₂F | H | 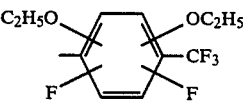 | 0 | NMR Oil (3-H,Pyr.) 7.70 ppm (s,1H) (CDCl₃/TMS) |
| 34 | H | CCl₂F | H | 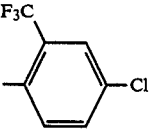 2-CF₃-4-Cl-phenyl | 2 | Fp 61–65° C. |
| 35 | H | CCl₂F | H | 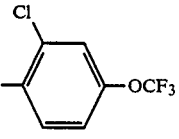 2-Cl-4-OCF₃-phenyl | 2 | Fp 117–124° C. |
| 36 | H | CCl₂F | H | 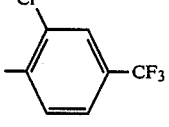 2-Cl-4-CF₃-phenyl | 2 | Fp 132–137° C. |
| 37 | H | CF₃ | H | 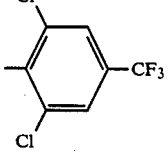 2,6-dichloro-4-CF₃-phenyl | 2 | Fp 57–63° C. |

-continued
| Example No. | R¹ | R² | R³ | Ar | n | Physical properties |
|---|---|---|---|---|---|---|
| 38 | H | CF₃ | H | 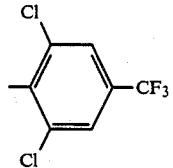 | 1 | Fp 86–92° C. |
| 39 | H | CCl₂F | H | 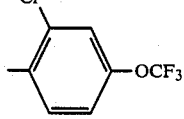 | 1 | Fp 45–55° C. |
| 40 | H | —CF₂—CCl₂F | H | 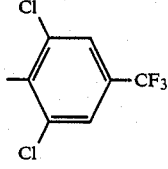 | 0 | Fp 117–119° C. |
| 41 | H | CCl₂F | H | 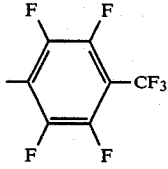 | 0 | NMR: Oil (3-H,Pyr.) 7.73 ppm (s,1H) (CDCl₃/TMS) |
| 42 | CH₃ | CCl₂F | H | 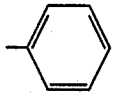 | 0 | Fp 69–70° C. |
| 43 | CH₃ | CCl₂F | C₂H₅CO | 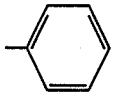 | 0 | Fp 194° C. |
| 44 | CH₃ | CCl₂F | H | 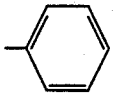 | 2 | Fp 94–95° C. |
| 45 | CH₃ | CCl₂F | H | 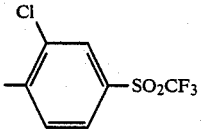 | 0 | Fp 108–110° C. |
| 46 | CH₃ | CCl₂F | C₂H₅CO |  | 1 | Fp 174° C. |
| 47 | CH₃ | CCl₂F | C₂H₅CO | 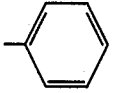 | 2 | Fp 208° C. |
| 48 | CH₃ | CCl₂F | H | 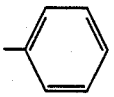 | 1 | NMR: Oil 3-CH₃ (Pyr.), S, 2.27 ppm (CDCl₃/TMS) |

-continued
| Example No. | R¹ | R² | R³ | Ar | n | Physical properties |
|---|---|---|---|---|---|---|
| 49 | $CH_3$ | $CCl_2F$ | $C_2H_5CO$ | 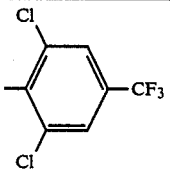 | 0 | Fp 128–130° C. |
| 50 | $CH_3$ | $CCl_2F$ | $C_2H_5CO$ | 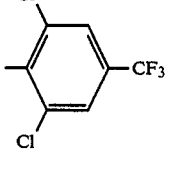 | 2 | Fp 179° C. |
| 51 | $CH_3$ | $CCl_2F$ | H | 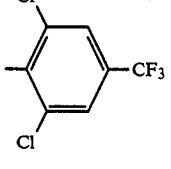 | 1 | Fp 63–64° C. |
| 51a | H | $CClF_2$ | H | 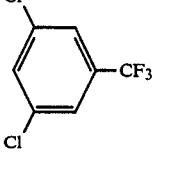 | 0 | |
| 52 | $(CH_3)_3C$ | $CCl_2F$ | H | 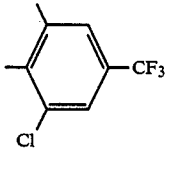 | 0 | Fp 140–144° C. |
| 53 | $CH_3$ | $CCl_3$ | H | 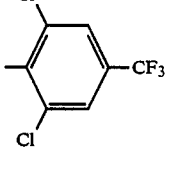 | 0 | Fp 150–152° C. |
| 54 | $CH_3$ | $CF_3$ | H | 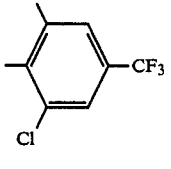 | 0 | Fp 147° C. |
| 55 | $CH_3$ | 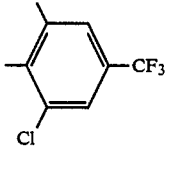 | H | 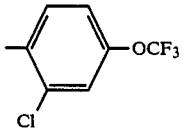 | 0 | Fp 58–82° C. |
| 56 | $CH_3$ | $CCl_2F$ | H | 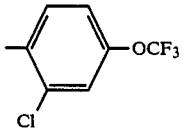 | 0 | Fp 58–61° C. |

-continued

| Example No. | R¹ | R² | R³ | Ar | n | Physical properties |
|---|---|---|---|---|---|---|
| 57 | CH₃ | CCl₂F | H | 2,6-dichloro-4-(SO₂CF₃)phenyl | 0 | Fp 78–80° C. |
| 58 | H | CH₃ | H | 2,4,6-trichlorophenyl | 0 | Fp 114° C. |
| 59 | H | CH₃ | C₂H₅O | 2,4,6-trichlorophenyl | 0 | Fp 92–95° C. (decomp.) |
| 60 | H | CH₃ | C₂H₅O | 2,4,6-trichlorophenyl | 2 | Fp 146–150° C. |
| 61 | H | CH₃ | H | 2,6-dichloro-4-CF₃-phenyl | 2 | Fp 60–65° C. |
| 62 | H | CH₃ | H | 2,4,6-trichlorophenyl | 2 | FP 170–171° C. |
| 63 | H | C₂H₅ | H | 2,6-dichloro-4-CF₃-phenyl | 0 | Fp 81–82° C. |
| 64 | H | (CH₃)₂CH— | H | 2,6-dichloro-4-CF₃-phenyl | 0 | Fp 77–79° C. |
| 65 | H | C₆H₅ | H | 2,6-dichloro-4-CF₃-phenyl | 0 | Fp 124–127° C. |

-continued
| Example No. | R¹ | R² | R³ | Ar | n | Physical properties |
|---|---|---|---|---|---|---|
| 66 | CH₃ | CH₃ | H | 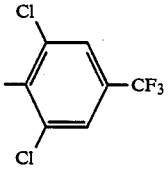 | 0 | Fp 54–57° C. |
| 67 | CH₃ | C₂H₅ | H | 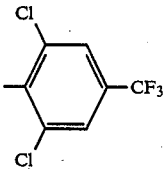 | 0 | Fp 109–110° C. |
| 68 | H | CCl₂F | H | 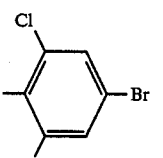 | 0 | Fp 92–94° C. |
| 69 | H | CCl₂F | H | 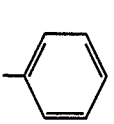 | 0 | Fp 85–89° C. |
| 70 | H | CCl₂F | H | 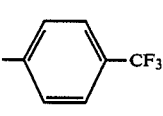 | 0 | Fp 70° C. |
| 71 | H | CCl₂F | H | 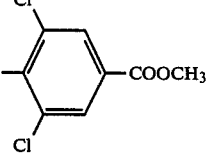 | 0 | Fp 140–144° C. |
| 72 | H | CCl₂F | H | 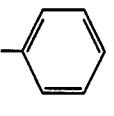 | 2 | Fp 107–110° C. |
| 73 | H | CCl₂F | H | 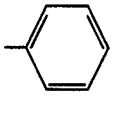 | 1 | Fp 75–77° C. |
| 74 | H | CCl₂F | C₂H₅O | 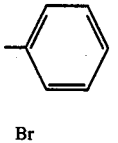 | 0 | Fp 88–90° C. |
| 75 | H | CCl₂F | H | 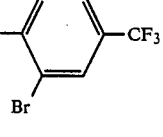 | 0 | Fp 80–83° C. |

-continued

| Example No. | R¹ | R² | R³ | Ar | n | Physical properties |
|---|---|---|---|---|---|---|
| 76 | H | CCl₂F | H | 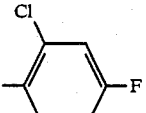 2-Cl, 4-F phenyl | 0 | Fp 68–72° C. |
| 77 | H | CCl₂F | H | 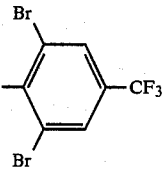 2,6-Br₂-4-CF₃ phenyl | 2 | Fp 104–106° C. |
| 78 | H | CCl₂F | H | 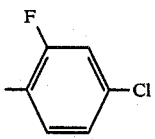 2-F, 4-Cl phenyl | 0 | NMR: Oil, 7.60 ppm (s,1H) 4.36 ppm (s,2H) (CDCl₃/TMS) |
| 79 | H | CCl₂F | H | 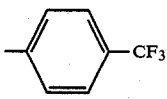 4-CF₃ phenyl | 2 | Fp 128–132° C. |
| 80 | H | CCl₂F | H | 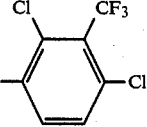 2,6-Cl₂-3-CF₃ phenyl | 0 | NMR: Oil, 7.61 ppm (s,1H) 4.26 ppm (s,2H) (CDCl₃/TMS) |
| 81 | H | CCl₂F | H | 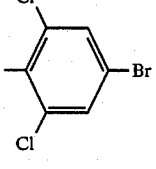 2,6-Cl₂-4-Br phenyl | 2 | Fp 100–101° C. |
| 82 | H | CCl₂F | H | 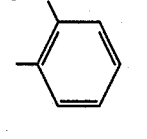 2-OCF₃ phenyl | 0 | NMR: Oil, 7.57 ppm (s,1H) 4.31 ppm (s,2H) (CDCl₃/TMS) |
| 83 | H | CF₃ | CH₃ | 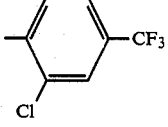 2,6-Cl₂-4-CF₃ phenyl | 0 | Fp 50–60° C. |
| 84 | H | CF₃ | H | 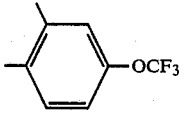 2-Cl, 4-OCF₃ phenyl | 0 | Fp 112–113° C. |
| 85 | H | CF₃ | H | 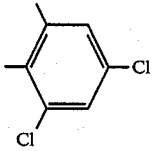 2,4,6-Cl₃ phenyl | 0 | Fp 90–91° C. |

-continued
| Example No. | R¹ | R² | R³ | Ar | n | Physical properties |
|---|---|---|---|---|---|---|
| 86 | H | CH₃ | H | 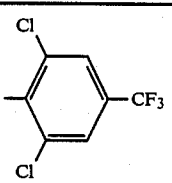 | 1 | Fp 179–182° C. |
| 87 | CH₃ | CH₃ | H | 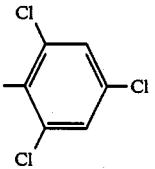 | 0 | Fp 128–131° C. |
| 88 | CH₃ | C₂H₅ | H | 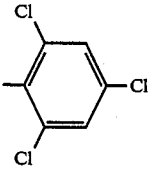 | 0 | Fp 121–123° C. |
| 89 | CH₃ | (CH₃)₂CH— | H | 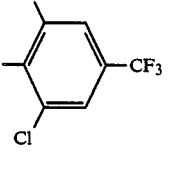 | 0 | Fp 100–101° C. |
| 90 | H | CCl₂F | H | 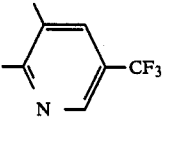 | 0 | NMR: Oil 7.7 ppm (s,1H) 8.2 ppm (1H) 8.6 ppm (1H) (CDCl₃/TMS) |
| 91 | CH₃ | CF₃ | H | 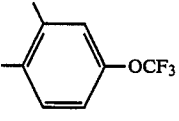 | 0 | Fp 67–70° C. |
| 92 | CH₃ | CF₃ | H | 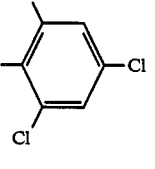 | 0 | Fp 122–125° C. |
| 93 | H | CCl₂F | H | 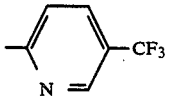 | 2 | Fp 102–110° C. |
| 94 | H | CCl₂F | H | 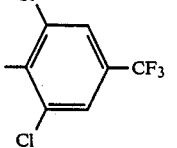 | 0 | Fp 68–74° C. |

-continued
| Example No. | R¹ | R² | R³ | Ar | n | Physical properties |
|---|---|---|---|---|---|---|
| 95 | H | CCl₂F | H | 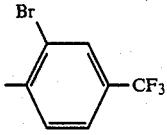 | 0 | Fp 60–70° C. |
| 96 | CH₃ | CF₃ | COC₂H₅ | 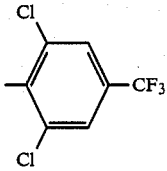 | 0 | Fp 138° C. |
| 97 | H | CF₃ | H | 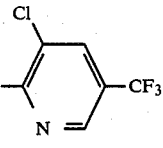 | 0 | Fp 67–68° C. |
| 98 | CH₃ | CCl₂F | H | 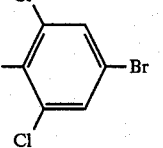 | 0 | Fp. 133–134° C. |
| 99 | CH₃ | CClF₂ | H | 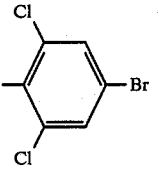 | 0 | Fp. 132–134° C. |
| 100 | CH₃ | CF₃ | H | 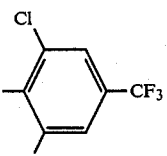 | 2 | Fp. 150–152° C. |
| 101 | CH₃ | CCl₂F | H | 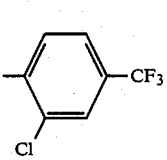 | 1 | Fp. 135–138° C. |
| 102 | CH₃ | CCl₂F | H | 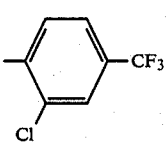 | 2 | Fp. 58–61° C. |
| 103 | CH₃ | CF₃ | H | 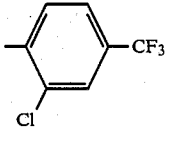 | 1 | Fp. 147° C. |

-continued
| Example No. | R¹ | R² | R³ | Ar | n | Physical properties |
|---|---|---|---|---|---|---|
| 104 | CH₃ | CF₃ | H | 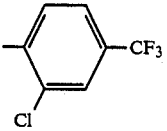 | 2 | Fp. 103–105° C. |
| 105 | CH₃ | CClF₂ | H | 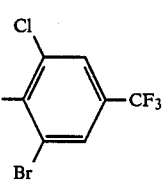 | 0 | Fp. 114–116° C. |
| 106 | CH₃ | CF₃ | H | 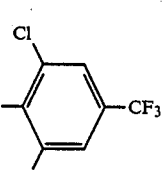 | 1 | Fp. 157–159° C. |
| 107 | CH₃ | CClF₂ | H | 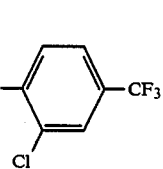 | 0 | NMR: Oil 3-CH₃ (Pyr.) (s,2.30 ppm) (CDCl₃/TMS) |
| 108 | CH₃ | CClF₂ | H | 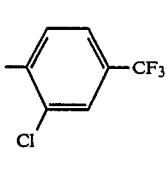 | 1 | Fp. 118–122° C. |
| 109 | CH₃ | CClF₂ | H | 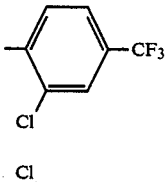 | 2 | Fp. 59–61° C. |
| 110 | CH₃ | CClF₂ | H | 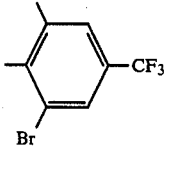 | 1 | Fp. 76–80° C. |
| 111 | CH₃ | CClF₂ | H | 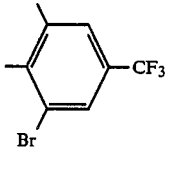 | 2 | Fp. 143–144° C. |
| 112 | CH₃ | CClF₂ | H | 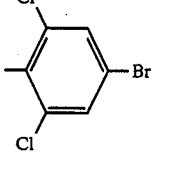 | 2 | Fp. 184–185° C. |

-continued
| Example No. | R¹ | R² | R³ | Ar | n | Physical properties |
|---|---|---|---|---|---|---|
| 113 | CH₃ | CF₃ | H | 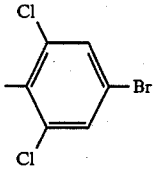 | 2 | Fp. 135–138° C. |
| 114 | CH₃ | CClF₂ | H | 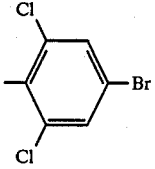 | 2 | Fp. 154–155° C. |
| 115 | CH₃ | CCl₂F | H | 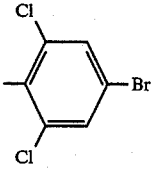 | 1 | Fp. 168–170° C. |
| 116 | CH₃ | CF₃ | H | 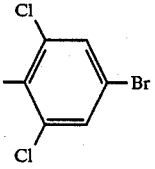 | 1 | Fp. 170° C. |
| 117 | CH₃ | CClF₂ | H | 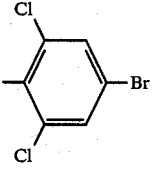 | 1 | Fp. 82–85° C. |
| 118 | CH₃ | CCl₂F | CO—C₂H₅ | 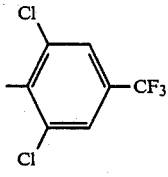 | 1 | Fp. 174° C. |
| 119 | CH₃ | CCl₂F | H | 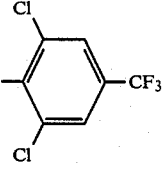 | 2 | Fp. 145° C. |
| 120 | CH₃ | CF₃ | H | 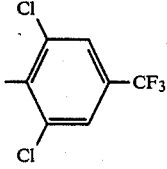 | 1 | Fp. 144–149° C. |
| 121 | CH₃ | CCl₂F | H | 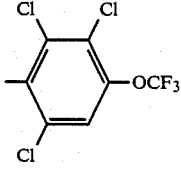 | 0 | Fp. 102–110° C. |

-continued
| Example No. | R¹ | R² | R³ | Ar | n | Physical properties |
|---|---|---|---|---|---|---|
| 122 | CH₃ | CCl₂F | H | 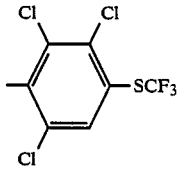 | 0 | Fp. 80–96° C. |
| 123 | CH₃ | CF₃ | H | 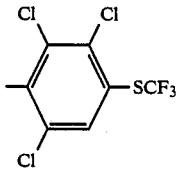 | 0 | Fp. 118–121° C. |
| 124 | CH₃ | CCl₂F | H | 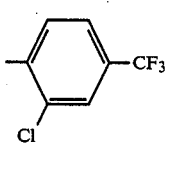 | 0 | Fp. 75–77° C. |
| 125 | CH₃ | CF₃ | H | 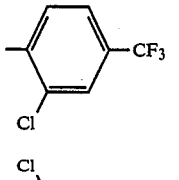 | 0 | Fp. 83° C. |
| 126 | CH₃ | CCl₂F | H | 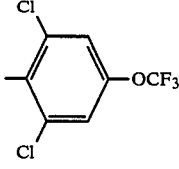 | 0 | Fp. 95–97° C. |
| 127 | CH₃ | CF₃ | H | 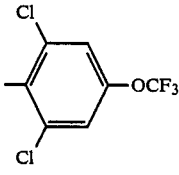 | 0 | Fp. 100–101° C. |
| 128 | C₂H₅ | CCl₂F | H | 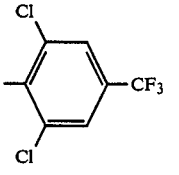 | 0 | Fp. 105–108° C. |
| 129 | C₂H₅ | CF₃ | H | 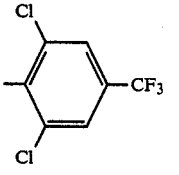 | 0 | Fp. 113–116° C. |
| 130 | C₂H₅ | CCl₂F | H | 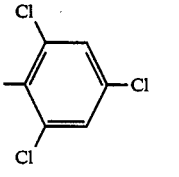 | 0 | Fp. 89–93° C. |

-continued

| Example No. | R¹ | R² | R³ | Ar | n | Physical properties |
|---|---|---|---|---|---|---|
| 131 | C₂H₅ | CF₃ | H | 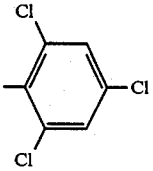 2,4-dichlorophenyl | 0 | Fp. 76–78° C. |
| 132 | CH₃ | CF₃ | H | 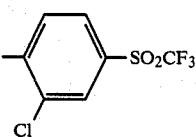 3-Cl, 4-SO₂CF₃ phenyl | 0 | NMR: Oil, 3-CH₃ (Pyr.), s, 2.30 ppm (CDCl₃/TMS) |
| 133 | CH₃ | CF₃ | COC₂H₅ | 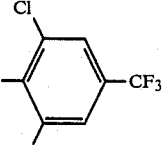 2,6-dichloro-4-CF₃ phenyl | 1 | Fp. 135–137° C. |
| 134 | CH₃ | CF₃ | COC₂H₅ | 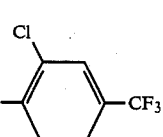 2,6-dichloro-4-CF₃ phenyl | 2 | Fp. 132–133° C. |
| 135 | CH₃ | CF₃ | H | 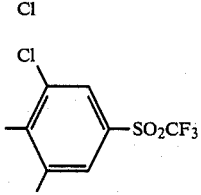 3,5-dichloro-4-SO₂CF₃ phenyl | 0 | Fp 160–169° C. |
| 136 | CH₃ | CF₃ | H | 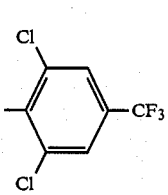 2,6-dichloro-4-CF₃ phenyl | 2 | Fp. 147–148° C. |
| 137 | CH₃ | CF₂Cl | H | 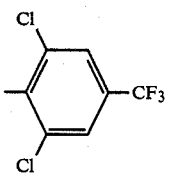 2,6-dichloro-4-CF₃ phenyl | 0 | Fp. 63–65° C. |
| 138 | CH₃ | CF₃ | COCH₃ | 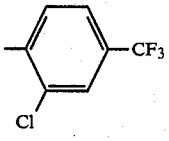 3-Cl, 4-CF₃ phenyl | 0 | Fp. 157–159° C. |
| 139 | CH₃ | CF₃ | H | 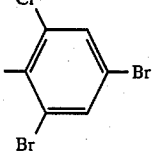 2-Cl, 4,5-dibromo phenyl | 0 | Fp. 143° C. |

-continued

| Example No. | R¹ | R² | R³ | Ar | n | Physical properties |
|---|---|---|---|---|---|---|
| 140 | $C_2H_5$ | $CCl_2F$ | $COCH_3$ | 2,4,6-trichlorophenyl | 0 | Fp. 158–160° C. |
| 141 | $C_2H_5$ | $CF_3$ | $COCH_3$ | 2,4,6-trichlorophenyl | 0 | Fp. 178–180° C. |
| 142 | $CH_3$ | $CCl_2F$ | H | 2-Cl-6-Br-4-$CF_3$-phenyl | 0 | Fp. 105–107° C. |
| 143 | $CH_3$ | $CF_3$ | H | 2-Cl-6-Br-4-$CF_3$-phenyl | 0 | Fp. 136–137° C. |
| 144 | $CH_3$ | $CF_3$ | H | 2,6-diCl-4-Br-phenyl | 0 | Fp. 137–138° C. |
| 145 | $C_2H_5$ | $CF_3$ | $COCH_3$ | 2,4,6-trichlorophenyl | 1 | Fp. 62–64° C. |
| 146 | $C_2H_5$ | $CF_3$ | $COCH_3$ | 2,4,6-trichlorophenyl | 2 | Fp. 140–141° C. |
| 147 | $C_2H_5$ | $CCl_2F$ | $COC_2H_5$ | 2,4,6-trichlorophenyl | 0 | Fp. 120–121° C. |
| 148 | $C_2H_5$ | $CCl_2F$ | $COC_2H_5$ | 2,4,6-trichlorophenyl | 1 | NMR: Oil, 3-$CH_3$ (Pyr.) (t,1.07 ppm) 3-$CH_2$ (Pyr.) (q,2.26 (CDCl$_3$/TMS) |

-continued
| Example No. | R¹ | R² | R³ | Ar | n | Physical properties |
|---|---|---|---|---|---|---|
| 149 | $C_2H_5$ | $CCl_2F$ | $COC_2H_5$ | 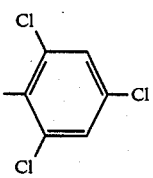 | 2 | Fp. 91–93° C. |
| 150 | $C_2H_5$ | $CF_3$ | H | 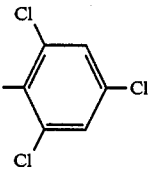 | 1 | Fp. 146–147° C. |
| 151 | $C_2H_5$ | $CF_3$ | H | 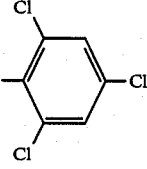 | 2 | Fp. 91–92° C. |
| 152 | $C_2H_5$ | $CCl_2F$ | H | 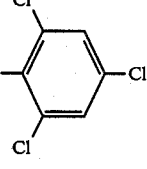 | 1 | Fp. 138–140° C. |
| 153 | $C_2H_5$ | $CCl_2F$ | H | 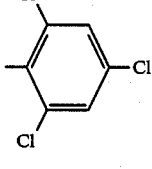 | 2 | Fp. 60–61° C. |
| 154 | $CH_3$ | $CClF_2$ | H | 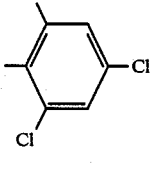 | 0 | Fp. 130–131° C. |
| 155 | $CH_3$ | $CClF_2$ | $COC_2H_5$ | 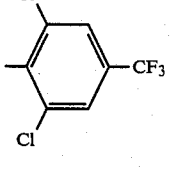 | 0 | Fp. 135° C. |
| 156 | $CH_3$ | $CClF_2$ | $COC_2H_5$ | 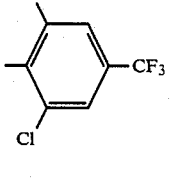 | 1 | Fp. 144–145° C. |

-continued
| Example No. | R¹ | R² | R³ | Ar | n | Physical properties |
|---|---|---|---|---|---|---|
| 157 | CH₃ | CClF₂ | COC₂H₅ | 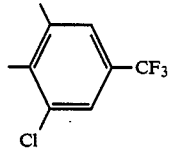 2,6-Cl₂-4-CF₃-phenyl | 2 | Fp. 144° C. |
| 158 | CH₃ | CF₃ | COC₂H₅ | 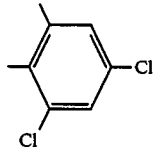 2,4,6-Cl₃-phenyl | 0 | Fp. 164° C. |
| 159 | CH₃ | CCl₂F | COC₂H₅ | 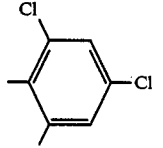 2,4,6-Cl₃-phenyl | 0 | Fp. 144–146° C. |
| 160 | CH₃ | CClF₂ | COC₂H₅ | 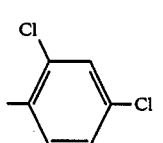 2,4,6-Cl₃-phenyl | 0 | Fp. 131° C. |
| 161 | CH₃ | CClF₂ | H | 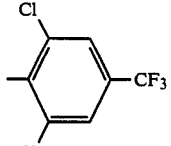 2,6-Cl₂-4-CF₃-phenyl | 1 | Fp. 63–67° C. |
| 162 | CH₃ | CClF₂ | H | 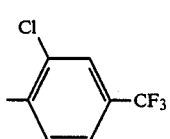 2,6-Cl₂-4-CF₃-phenyl | 2 | Fp. 120–128° C. |
| 163 | CH₃ | CF₃ | COC₂H₅ | 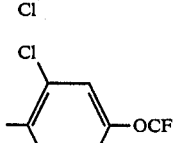 2,6-Cl₂-4-OCF₃-phenyl | 0 | Fp. 128–130° C. |
| 164 | CH₃ | CCl₂F | COC₂H₅ | 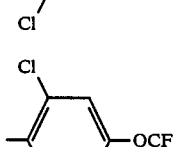 2,6-Cl₂-4-OCF₃-phenyl | 0 | Fp. 102° C. |
| 165 | CH₃ | CClF₂ | H | 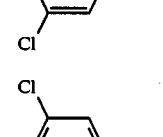 2,6-Cl₂-4-OCF₃-phenyl | 0 | Fp. 111–112° C. |

-continued
| Example No. | R¹ | R² | R³ | Ar | n | Physical properties |
|---|---|---|---|---|---|---|
| 166 | $CH_3$ | $CF_3$ | $COC_2H_5$ | 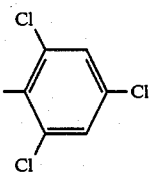 | 0 | Fp. 118–124° C. |
| 167 | $CH_3$ | $CF_3$ | $COC_2H_5$ | 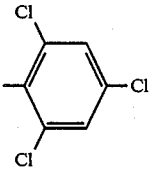 | 2 | Fp. 100–102° C. |
| 168 | $CH_3$ | $CCl_2F$ | $COC_2H_5$ | 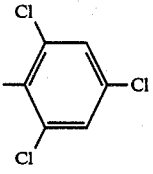 | 1 | Fp. 102–103° C. |
| 169 | $CH_3$ | $CCl_2F$ | $COC_2H_5$ | 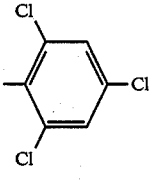 | 2 | Fp. 168–169° C. |
| 170 | $CH_3$ | $CClF_2$ | $COC_2H_5$ | 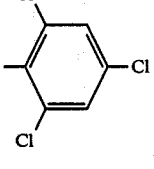 | 1 | Fp. 161–163° C. |
| 171 | $CH_3$ | $CClF_2$ | $COC_2H_5$ | 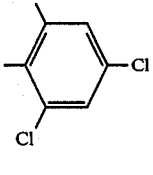 | 2 | Fp. 111–113° C. |
| 172 | $CH_3$ | $CClF_2$ | $COC_2H_5$ | 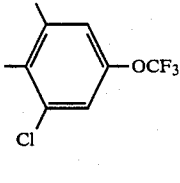 | 0 | Fp. 108–109° C. |
| 173 | $CH_3$ | $CF_3$ | H | 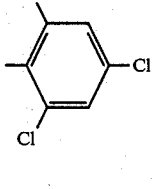 | 1 | Fp. 178–180° C. |

-continued
| Example No. | $R^1$ | $R^2$ | $R^3$ | Ar | n | Physical properties |
|---|---|---|---|---|---|---|
| 174 | $CH_3$ | $CF_3$ | H | 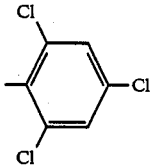 | 2 | Fp. 145–147° C. |
| 175 | $CH_3$ | $CCl_2F$ | H | 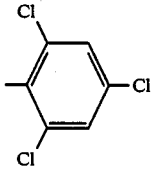 | 1 | Fp. 180–181° C. |
| 176 | $CH_3$ | $CCl_2F$ | H | 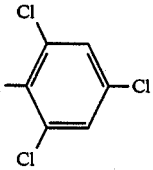 | 2 | Fp. 162–178° C. |
| 177 | $CH_3$ | $CClF_2$ | H | 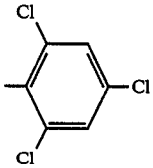 | 1 | Fp. 155–156° C. |
| 178 | $CH_3$ | $CClF_2$ | H | 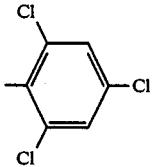 | 2 | Fp. 128–134° C. |
| 179 | $CH_3$ | $CF_3$ | $COC_2H_5$ | 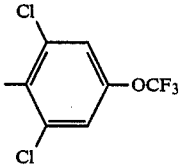 | 1 | Fp. 60–65° C. |
| 180 | $CH_3$ | $CF_3$ | $COC_2H_5$ | 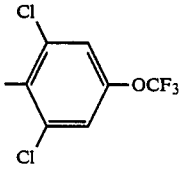 | 2 | Fp. 122–123° C. |
| 181 | $CH_3$ | $CCl_2F$ | $COC_2H_5$ | 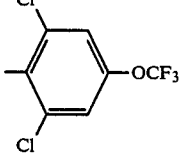 | 2 | Fp. 146–147° C. |
| 182 | $CH_3$ | $CCl_2F$ | $COC_2H_5$ | 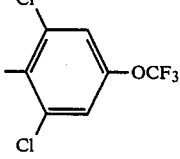 | 2 | Fp. 172° C. |

-continued

| Example No. | R¹ | R² | R³ | Ar | n | Physical properties |
|---|---|---|---|---|---|---|
| 183 | CH₃ | CClF₂ | COC₂H₅ | 2,6-Cl₂-4-OCF₃-C₆H₂ | 1 | Fp. 129–130° C. |
| 184 | CH₃ | CClF₂ | COC₂H₅ | 2,6-Cl₂-4-OCF₃-C₆H₂ | 2 | Fp. 151° C. |
| 185 | CH₃ | CF₃ | H | 2,6-Cl₂-4-OCF₃-C₆H₂ | 1 | Fp. 65–70° C. |
| 186 | CH₃ | CF₃ | H | 2,6-Cl₂-4-OCF₃-C₆H₂ | 2 | Fp. 121–123° C. |
| 187 | CH₃ | CCl₂F | H | 2,6-Cl₂-4-OCF₃-C₆H₂ | 1 | Fp. 72–76° C. |
| 188 | CH₃ | CCl₂F | H | 2,6-Cl₂-4-OCF₃-C₆H₂ | 2 | Fp. 72–76° C. |
| 189 | CH₃ | CClF₂ | H | 2,6-Cl₂-4-OCF₃-C₆H₂ | 1 | Fp. 63–67° C. |
| 190 | CH₃ | CClF₂ | H | 2,6-Cl₂-4-OCF₃-C₆H₂ | 2 | Fp. 114–115° C. |

-continued

| Example No. | R¹ | R² | R³ | Ar | n | Physical properties |
|---|---|---|---|---|---|---|
| 191 | CH₃ | —CH₂—CH₂—C₆H₅ | H | 2,6-Cl₂-4-CF₃-C₆H₂ | 0 | Fp. 108–110° C. |
| 192 | CH₃ | CH₃ | H | 2,6-Cl₂-4-CF₃-C₆H₂ | 1 | Fp. 56–60° C. |
| 193 | CH₃ | CH₃ | H | 2,6-Cl₂-4-CF₃-C₆H₂ | 2 | Fp. 179–181° C. |
| 194 | CH₃ | C₂H₅ | H | 2,6-Cl₂-4-CF₃-C₆H₂ | 1 | Fp. 62–66° C. |
| 195 | CH₃ | C₂H₅ | H | 2,6-Cl₂-4-CF₃-C₆H₂ | 2 | Fp. 140–156° C. |
| 196 | (CH₃)₃C | CH₃ | H | 2,6-Cl₂-4-CF₃-C₆H₂ | 0 | Fp. 81° C. |
| 197 | CH₃ | 4-Cl-C₆H₄ | H | 2,6-Cl₂-4-CF₃-C₆H₂ | 0 | Fp. 72° C. |
| 198 | CH₃ | 4-Cl-C₆H₄ | H | 2,6-Cl₂-4-CF₃-C₆H₂ | 2 | Fp. 73–78° C. |
| 199 | H | C₂H₅ | H | 3,5-Cl₂-pyridin-2-yl | 0 | Fp. 61° C. |

-continued
| Example No. | R¹ | R² | R³ | Ar | n | Physical properties |
|---|---|---|---|---|---|---|
| 200 | $CH_3$ | $CCl_2F$ | H | 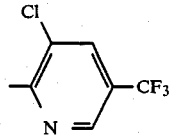 | 2 | NMR: Oil, 7.8 (s,1H) 8.2 (1H) 8.6 (1H) ($CDCl_3$/TMS) |
| 201 | $CH_3$ | $CF_3$ | H | 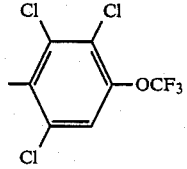 | 0 | Fp. 119–123° C. |
| 202 | H | $CF_2Cl$ | H | 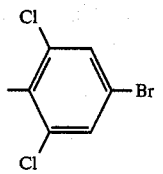 | 2 | Fp. 148–150° C. |
| 203 | H | $CF_2Cl$ | H | 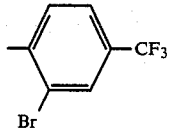 | 0 | Fp. 96–98° C. |
| 204 | H | $CF_2Cl$ | H | 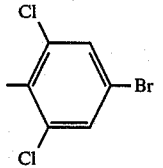 | 1 | Fp. 110–115° C. |
| 205 | H | $CF_3$ | H | 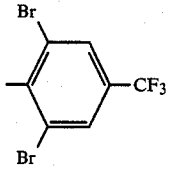 | 0 | Fp. 126° C. |
| 206 | H | $CF_3$ | H | 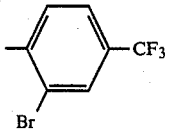 | 2 | Fp. 144° C. |
| 207 | H | $CCl_2F$ | H | 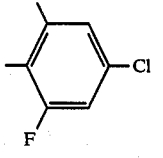 | 0 | NMR: 7.63 ppm (s,1H) 4.35 ppm (s broad 2H) |
| 208 | H | $CF_3$ | H | 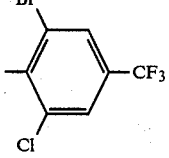 | 1 | Fp. 82–88° C. |

-continued

| Example No. | R¹ | R² | R³ | Ar | n | Physical properties |
|---|---|---|---|---|---|---|
| 209 | H | $CF_3$ | H | 2,3,5-trichloro-6-SCF₃-phenyl | 0 | Fp. 110–111° C. |
| 210 | H | $CCl_2F$ | H | 2,6-dichloro-4-CF₃-phenyl (Br instead of Cl at 2) — 2-Br, 6-Cl, 4-CF₃-phenyl | 0 | Fp. 110–115° C. |
| 211 | H | $CCl_2F$ | H | 2,5-dibromo-6-OCF₃-phenyl | 0 | Fp. 73° C. |
| 212 | H | $CCl_2F$ | H | 2-Cl, 6-Br, 4-CF₃-phenyl | 2 | Fp. 145° C. |
| 213 | H | $CCl_2F$ | H | 2-Cl, 6-Br, 4-CF₃-phenyl | 1 | Fp. 99–112° C. |
| 214 | H | $CCl_2F$ | H | 2,5-dibromo-6-OCF₃-phenyl | 2 | Fp. 132° C. |
| 215 | H | $CCl_2F$ | H | 2-Cl, 6-Br, 4-F-phenyl | 0 | Fp. 119° C. |
| 216 | H | $CF_2Cl$ | H | 2-Cl, 6-Br, 4-CF₃-phenyl | 0 | Fp. 116–118° C. |
| 217 | H | $CF_2Cl$ | H | 2-Cl, 6-Br, 4-CF₃-phenyl | 1 | Fp. 117–118° C. |

-continued
| Example No. | R¹ | R² | R³ | Ar | n | Physical properties |
|---|---|---|---|---|---|---|
| 218 | H | CCl₂F | H | 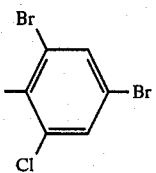 2-Cl, 3-Br, 5-Br phenyl | 0 | Fp. 84–86° C. |
| 219 | H | CF₂Cl | H | 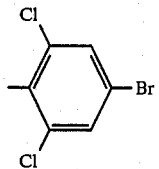 2,3-diCl, 5-Br phenyl | 0 | Fp. 87–88° C. |
| 220 | H | 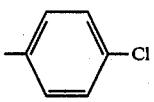 4-Cl phenyl | H | 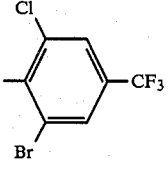 2-Cl, 3-Br, 5-CF₃ phenyl | 0 | Fp. 150–156° C. |
| 221 | H | CCl₂F | H | 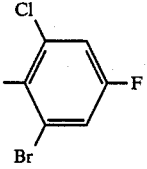 2-Cl, 3-Br, 5-F phenyl | 2 | Fp. 80–85° C. |
| 222 | H | CCl₂F | H | 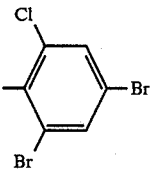 2-Cl, 3-Br, 5-Br phenyl | 2 | Fp. 165–168° C. |
| 223 | H | 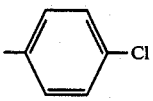 4-Cl phenyl | H | 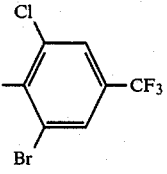 2-Cl, 3-Br, 5-CF₃ phenyl | 2 | Fp. 170–175° C. |
| 224 | H | CCl₂F | H | 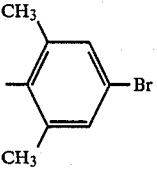 2,3-diCH₃, 5-Br phenyl | 0 | Fp. 125–133° C. |
| 225 | H | CCl₂F | H | 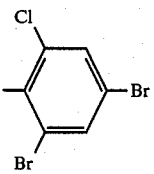 2-Cl, 3-Br, 5-Br phenyl | 1 | Fp. 102–107° C. |

-continued

| Example No. | R¹ | R² | R³ | Ar | n | Physical properties |
|---|---|---|---|---|---|---|
| 226 | H | CCl₂F | H | 3,5-dichloro-4-...-bromophenyl (Cl, Cl, Br) | 1 | Fp. 70–77° C. |
| 227 | H | CCl₂F | H | 3,5-dimethyl-4-...-chlorophenyl | 0 | Fp. 134–136° C. |
| 228 | H | CCl₂F | H | 2-bromo-4-fluorophenyl | 0 | Fp. 70° C. |
| 229 | H | CF₂Cl | H | 3-bromo-5-chloro-4-...-(trifluoromethyl)phenyl | 2 | Fp. 112–120° C. |
| 230 | H | CCl₂F | H | 4-chloro-2-(trifluoromethoxy)phenyl | 0 | NMR: Oil, 7.62 ppm (s,1H) 4.24 ppm (s,2H) (CDCl₃/TMS) |
| 231 | H | CClF₂ | H | 3,5-dichloro-4-...-(trifluoromethoxy)phenyl | 0 | Fp. 103–108° C. |
| 232 | H | CClF₂ | H | 3,5-dibromo-4-...-(trifluoromethyl)phenyl | 0 | Fp. 119–122° C. |
| 233 | H | CClF₂ | H | 3,5-dibromo-4-...-(trifluoromethyl)phenyl | 2 | Fp. 128–133° C. |
| 234 | H | CClF₂ | H | 3,5-dichloro-4-...-(trifluoromethoxy)phenyl | 1 | Fp. 78–98° C. |

-continued

| Example No. | R¹ | R² | R³ | Ar | n | Physical properties |
|---|---|---|---|---|---|---|
| 235 | H | CClF₂ | H | 3,5-dichloro-4-(OCF₃)phenyl | 2 | Fp. 98–103° C. |
| 236 | H | CCl₂F | H | 3,5-dibromo-4-Cl phenyl | 0 | Fp. 88–90° C. |
| 237 | H | CCl₂F | H | 2,3-dichloro-4,6-dibromophenyl | 0 | Fp. 80–85° C. |
| 238 | H | CCl₂F | H | 3-bromo-5-CF₃ phenyl | 1 | Fp. 106–111° C. |
| 239 | H | CCl₂F | H | 3-bromo-2-chloro-5-bromo-6-CH₃ phenyl | 0 | Fp. 109–113° C. |
| 240 | H | CCl₂F | H | 3-bromo-2-chloro-5-bromo-6-Cl phenyl | 0 | Fp. 113–116° C. |
| 241 | H | CCl₂F | H | 3-bromo-2-chloro-5-Cl-6-Br phenyl | 2 | Fp. 80° C. |
| 242 | H | CCl₂F | H | 2,3,5-trichloro-6-SCF₃ phenyl | 0 | Fp. 114–118° C. |
| 243 | H | CClF₂ | H | 3,5-dibromo-5-CF₃ phenyl | 1 | Fp. 63–70° C. |

-continued
| Example No. | R¹ | R² | R³ | Ar | n | Physical properties |
|---|---|---|---|---|---|---|
| 244 | H | CF₃ | H | 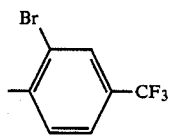 2-Br, 4-CF₃ | 0 | Fp. 94° C. |
| 245 | H | CCl₂F | H | 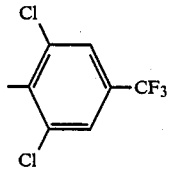 2,6-Cl₂, 4-CF₃ | 2 | Fp. 144–150° C. |
| 246 | H | CCl₂F | H | 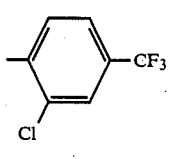 3-Cl, 4-CF₃ | 1 | Fp. 70–72° C. |
| 247 | H | CCl₂F | CH₃ | 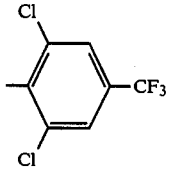 2,6-Cl₂, 4-CF₃ | 1 | Fp. 141–146° C. |
| 248 | H | CF₃ | COCH₃ | 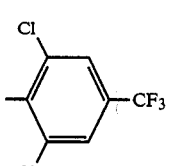 2,6-Cl₂, 4-CF₃ | 1 | Fp. 103° C. |
| 249 | H | CF₃ | H | 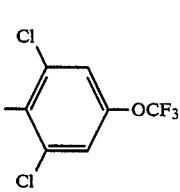 2,6-Cl₂, 4-OCF₃ | 0 | Fp. 131–132° C. |
| 250 | H | CF₃ | H | 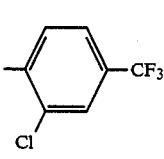 3-Cl, 4-CF₃ | 0 | Fp. 82–83° C. |
| 251 | H | CCl₂F | H | 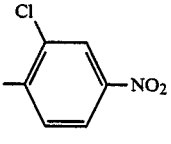 2-Cl, 4-NO₂ | 0 | Fp. 137–139° C. |
| 252 | H | CF₃ | H | 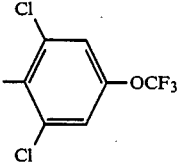 2,6-Cl₂, 4-OCF₃ | 1 | Fp. 55–57° C. |

-continued
| Example No. | R¹ | R² | R³ | Ar | n | Physical properties |
|---|---|---|---|---|---|---|
| 253 | H | CCl₂F | H | 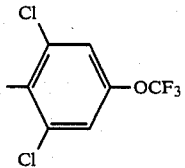 | 1 | Fp. 59–66° C. |
| 254 | H | CF₃ | H | 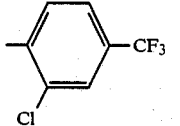 | 1 | Fp. 133° C. |
| 255 | H | CCl₂F | H | 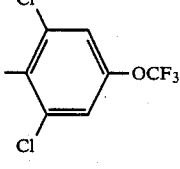 | 2 | Fp. 107–112° C. |
| 256 | H | CF₃ | H | 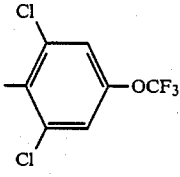 | 2 | Fp. 110–116° C. |
| 257 | H | CF₃ | H | 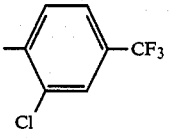 | 2 | Fp. 108–111° C. |
| 258 | H | CCl₂F | H | 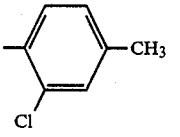 | 0 | Fp. 116–118° C. |
| 259 | H | CCl₂F | H | 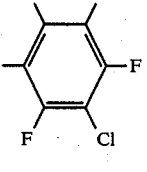 | 0 | Fp. 95–97° C. |
| 260 | H | 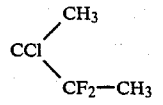 | H | 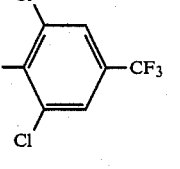 | 0 | Fp. 121° C. |
| 261 | H | CCl₂F | H | 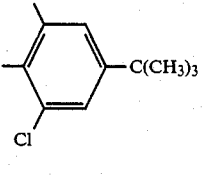 | 0 | Fp. 150–152° C. |

-continued
| Example No. | R¹ | R² | R³ | Ar | n | Physical properties |
|---|---|---|---|---|---|---|
| 262 | H | CCl₂F | H | 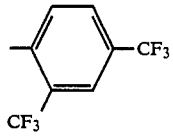 | 0 | Fp. 81–83° C. |
| 263 | H | CCl₂F | H | 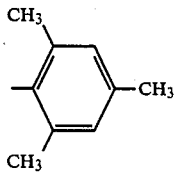 | 0 | Fp. 154–156° C. |
| 264 | H | CClF₂ | H | 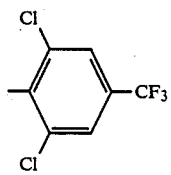 | 1 | Fp. 92–99° C. |
| 265 | H | CF₃ | H | 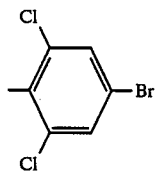 | 0 | Fp. 122–124° C. |
| 266 | H | CF₃ | H | 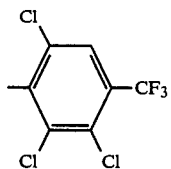 | 0 | Fp. 109–114° C. |
| 267 | H | CClF₂ | H | 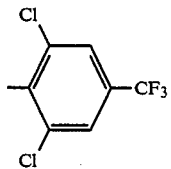 | 2 | Fp. 125–132° C. |
| 268 | H | CF₃ | CH₃ | 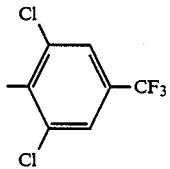 | 1 | Fp. 125–127° C. |
| 269 | H | CCl₂F | COCH₃ | 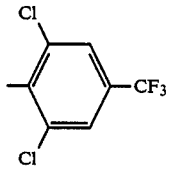 | 1 | Fp. 208–210° C. |
| 270 | H | CCl₂F | CH(CH₃)₂ | 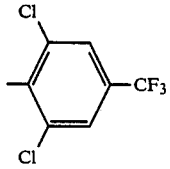 | 2 | NMR: Oil, 7.88 ppm (s,1H) 1.07 ppm (d,6H) (CDCl₃/TMS) |

-continued
| Example No. | R¹ | R² | R³ | Ar | n | Physical properties |
|---|---|---|---|---|---|---|
| 271 | H | CCl₂F | COCH₃ | 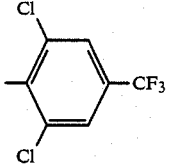 | 0 | Fp. 166–169° C. |
| 272 | H | CF₃ | H | 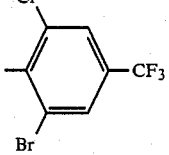 | 0 | Fp. 127–128° C. |
| 273 | H | CCl₂F | COCH₃ | 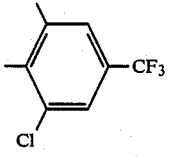 | 2 | Fp. 164–165° C. |
| 274 | H | CF₃ | H | 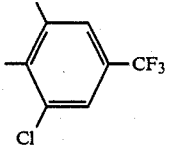 | 2 | Fp. 135–136° C. |
| 275 | H | CH(CH₃)₂ | H | 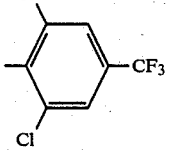 | 1 | Fp. 60–65° C. |
| 276 | H | CH₃ | H | 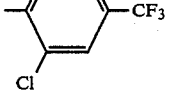 | 0 | Fp. 92° C. |
| 277 | H | C₂H₅ | H | 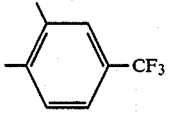 | 0 | Fp. 67–68° C. |
| 278 | H | CH(CH₃)₂ | H | 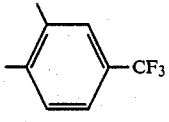 | 0 | Fp. 82–83° C. |
| 279 | H | C₂H₅ | H | 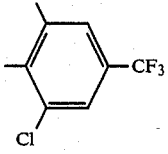 | 1 | Fp. 57–61° C. |

-continued
| Example No. | R¹ | R² | R³ | Ar | n | Physical properties |
|---|---|---|---|---|---|---|
| 280 | H | C₂H₅ | H | 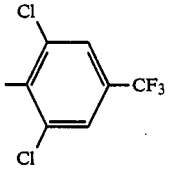 2,6-Cl₂-4-CF₃-phenyl | 2 | Fp. 130° C. |
| 281 | H | CH(CH₃)₂ | H | 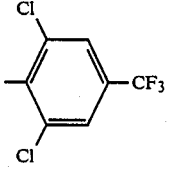 2,6-Cl₂-4-CF₃-phenyl | 2 | Fp. 142° C. |
| 282 | H | CH₃ | H | 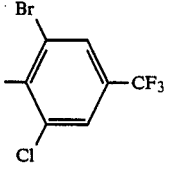 2-Br-6-Cl-4-CF₃-phenyl | 0 | Fp. 105° C. |
| 283 | H | C₂H₅ | H | 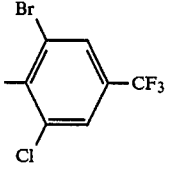 2-Br-6-Cl-4-CF₃-phenyl | 0 | Fp. 85° C. |
| 284 | H | CH₃ | H | 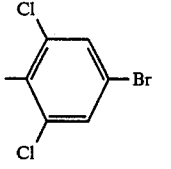 2,6-Cl₂-4-Br-phenyl | 0 | Fp. 110° C. |
| 285 | H | C₂H₅ | H | 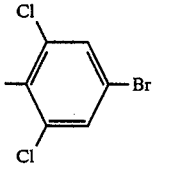 2,6-Cl₂-4-Br-phenyl | 0 | Fp. 72–73° C. |
| 286 | H | CH(CH₃)₂ | H | 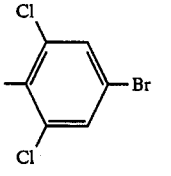 2,6-Cl₂-4-Br-phenyl | 0 | NMR: 2.24 ppm (d,6H) 3.95 ppm (s,1H) 7.57 ppm (s,1H) 7.66 ppm (s,2H) (CDCl₃/TMS) |
| 287 | H | 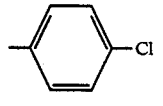 4-Cl-phenyl | H | 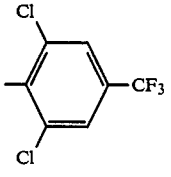 2,6-Cl₂-4-CF₃-phenyl | 0 | Fp. 155° C. |
| 288 | H | 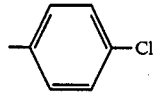 4-Cl-phenyl | H | 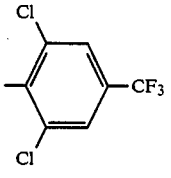 2,6-Cl₂-4-CF₃-phenyl | 2 | Fp. 178° C. |

-continued
| Example No. | R¹ | R² | R³ | Ar | n | Physical properties |
|---|---|---|---|---|---|---|
| 289 | H | CH₃ | H | 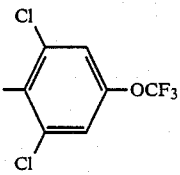 | 0 | Fp. 90° C. |
| 290 | H | C₂H₅ | H | 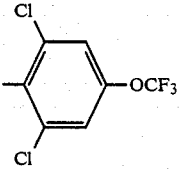 | 0 | Fp. 79° C. |
| 291 | H | CH₃ | H | 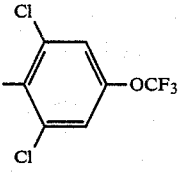 | 1 | Fp. 146° C. |
| 292 | H | CH₃ | H | 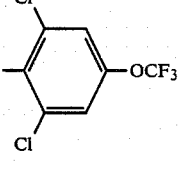 | 2 | Fp. 124° C. |
| 293 | H | C₂H₅ | H | 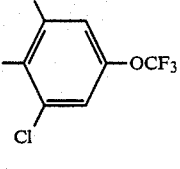 | 1 | Fp. 108–110° C. |
| 294 | H | C₂H₅ | H | 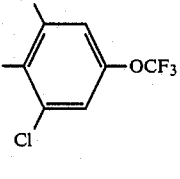 | 2 | Fp. 129° C. |
| 295 | H | CH(CH₃)₂ | H | 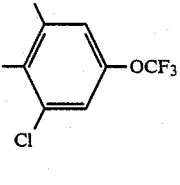 | 0 | Fp. 80° C. |
| 296 | H | CF₂CHFCl | H | 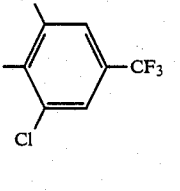 | 0 | Fp. 73° C. |

-continued

| Example No. | R¹ | R² | R³ | Ar | n | Physical properties |
|---|---|---|---|---|---|---|
| 297 | H | CH₂—CH₂—C₆H₅ | H | 2,6-Cl₂-4-CF₃-C₆H₂ | 0 | Fp. 68–69° C. |
| 298 | H | CCl₂F | H | 2,3,5-Cl₃-4-OCF₃-C₆H | 0 | Fp. 106–110° C. |
| 299 | H | CF₃ | H | 2,3,5-Cl₃-4-OCF₃-C₆H | 0 | Fp. 84–87° C. |
| 300 | H | CCl₂F | C₂H₅ | 2,6-Cl₂-4-CF₃-C₆H₂ | 0 | NMR: (3-H,Pyr.) 7.75 (s,1H) (CDCl₃/TMS) |
| 301 | H | CCl₂F | H | 2,6-F₂-4-CF₃-C₆H₂ | 0 | NMR: (3-H,Pyr.) 7.71 (s,1H) (CDCl₃/TMS) |
| 302 | H | CCl₂F | H | 2,6-Cl₂-3,5-F₂-4-CF₃-C₆ | 0 | Fp. 81–87° C. |
| 303 | H | CCl₂F | H | 2,6-Br₂-4-CH(CH₃)₂-C₆H₂ | 0 | Fp. 130–135° C. |
| 304 | H | CF₃ | H | 2,6-Br₂-4-CF₃-C₆H₂ | 2 | Fp. 145–147° C. |
| 305 | H | CF₃ | H | 2,6-Br₂-4-CF₃-C₆H₂ | 1 | Fp. 66–75° C. |

-continued

| Example No. | R¹ | R² | R³ | Ar | n | Physical properties |
|---|---|---|---|---|---|---|
| 306 | CH₃ | CF₃ | CH₃ | 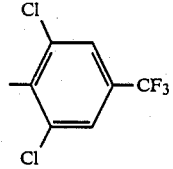 2,6-dichloro-4-CF₃-phenyl | 0 | Fp. 64–65° C. |
| 307 | CH₃ | CF₃ | CH₃ | 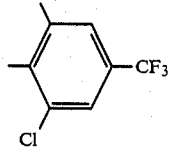 2,6-dichloro-4-CF₃-phenyl | 1 | Fp. 250° C. |
| 308 | CH₃ | CClF₂ | CH₃ | 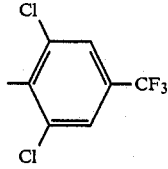 2,6-dichloro-4-CF₃-phenyl | 0 | Fp. 95–97° C. |
| 309 | CH₃ | CF₃ | CH₃ | 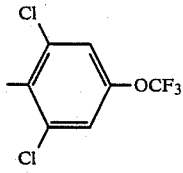 2,6-dichloro-4-OCF₃-phenyl | 0 | Fp. 80–82° C. |
| 310 | CH₃ | CF₃ | CH₃ | 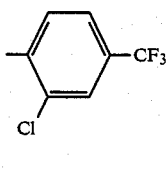 2-chloro-4-CF₃-phenyl | 0 | Fp. 68–69° C. |
| 311 | CH₃ | CCl₂F | CH₃ | 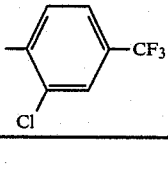 2-chloro-4-CF₃-phenyl | 0 | Oil |

USE EXAMPLES

The compounds shown below are employed as comparison compounds in the following use examples:

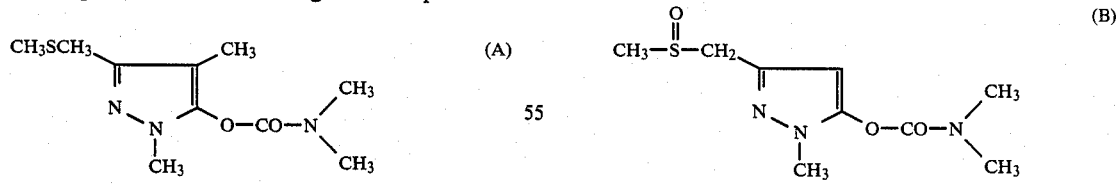

1,4-Dimethyl-5-[N,N-(dimethyl)-carbamolyloxy]-3-methylthiomethyl-pyrazole (known from DE-OS (German Published Specification) No. 2,912,494)     (A)

5-[N,N-(Dimethyl)-carbamoyloxy]-1-methyl-3-methylsulphinylmethyl-pyrazole (known from DE-OS (German Published Specification) No. 2,819,932)     (B)

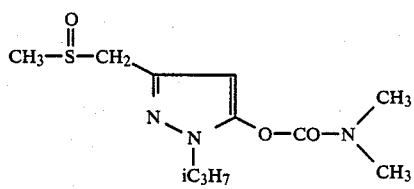

5-[N,N-(Dimethyl)-carbamoyloxy]-1-isopropyl-3-methylsulphinylmethyl-pyrazole (known from DE-OS (German Published Specification) No. 2,819,932)

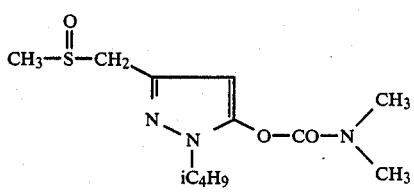

5-[N,N-(Dimethyl)-carbamoyloxy]-1-isobutyl-3-methylsulphinylmethyl-pyrazole (known from DE-OS (German Published Specification) No. 2,819,932)

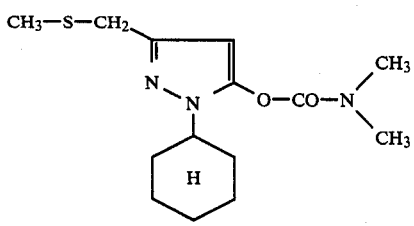

1-Cyclohexyl-5-[N,N-(dimethyl)-carbamoyloxy]-3-methylthiomethyl-pyrazole (known from DE-OS (German Published Specification) No. 2,839,270)

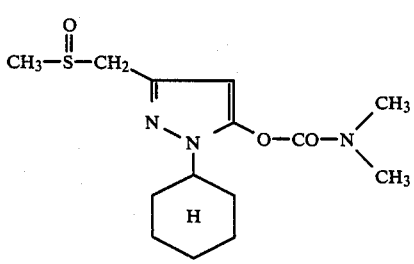

1-Cyclohexyl-5-[N,N-(dimethyl)-carbamoyloxy]-3-methylsulphinylmethyl-pyrazole (known from DE-OS (German Published Specification) No. 2,839,270)

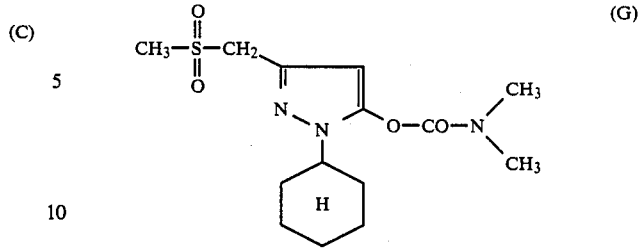

1-Cyclohexyl-5-[N,N-(dimethyl)-carbamoyloxy]-3-methylsulphonylmethyl-pyrazole (known from DE-OS (German Published Specification) No. 2,839,270)

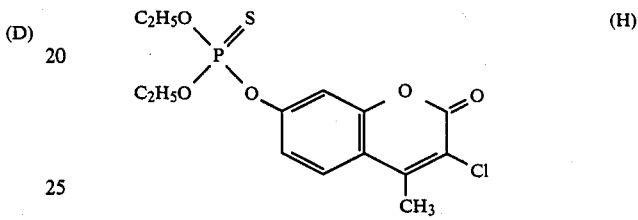

O,O-Diethyl O-(3-chloro-4-methyl-coumarin-7-yl)thionophosphate (known from "Pflanzenschutz und Schädlingsbekämpfung" ("Plant protection and combating pests"), K. H. Büchel; G. Thieme Verlag Stuttgart 1967, page 38).

EXAMPLE A

Phaedon larvae test

Solvent: 7 parts by weight of dimethylformamide
Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae), as long as the leaves are still moist.

After the specified periods of time, the destruction in % is determined. 100% means that all the larvae have been killed; 0% means that none of the larvae have been killed.

In this test, for example, the following compounds from the preparation examples show a superior activity compared to the prior art: 1, 5, 7, 10, 11, 13, 14, 15, 16, 17, 18, 24, 25, 29, 31, 49, 61, 62, 78, 70, 66, 63, 90, 22, 51a, 83, 92, 38, 37, 36, 77 and 247.

EXAMPLE B

Plutella test

Solvent: 7 parts by weight of dimethylformamide
Emulsifier: 1 part of weight of alkylaryl polyglycol ether.

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed.

In this test, for example, the following compounds from the preparation examples show a superior activity compared to the prior art: 3, 5, 10, 11, 12, 13, 16, 17, 21, 23, 25, 27, 29, 30, 31, 61, 68, 70, 90, 22, 51a, 83, 92, 38, 36, 77 and 247.

EXAMPLE C

Tetranychus test (resistant)

Solvent: 7 parts by weight of dimethylformamide
Emulsifier: 1 part of weight of alkylaryl polyglycol ether.

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, for example, the following compounds from the preparation examples show a superior activity compared to the prior art: 10, 11, 17, 21, 70, 66, 63, 90, 51a, 37.

EXAMPLE D

Critical concentration test/soil insects

Test insect: *Phorbia antiqua* maggots in the soil
Solvent: 3 parts by weight
Emulsifier: 1 part by weight alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show a superior action compared to the prior art: 3, 9, 10, 11, 12 and 66.

EXAMPLE E

Critical concentration test/root-systemic action

Test insect: *Phaedon cochleariae*
Solvent: 3 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all the test animals have been killed and 0% if just as many test insects are still alive as in the case of the untreated control.

In this test, for example, the following compounds from the preparation examples show a superior action compared to the prior art: 1, 3, 9, 10, 11, 12 and 66.

EXAMPLE F

Critical concentration test

Test nematode: *Meloidogyne incognita*
Solvent: 3 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, potatoes are sown in and the pots are kept at a greenhouse temperature of 18° C.

After six weeks, the potato roots are examined for cysts and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example the following compounds from the preparation examples show a superior action compared to the prior art: 12.

EXAMPLE G

LD$_{100}$ test

Test animals: *Blatta orientalis*
Solvent: Acetone.

2 parts by weight of active compound are taken up in 1,000 parts by volume of solvent. The solution thus obtained is diluted with further solvent to the desired concentration.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per m$^2$ of filterpaper varies, depending on the concentration of the active compound solution. The stated number of test animals is then introduced into the Petri dish, and the dish is covered with a glass lid.

The condition of the test animals is checked 3 days after the tests have been set up. The destruction is determined in %. 100% means that all of the test animals have been killed; 0% means that none of the test animals have been killed.

In this test, for example, the following compounds from the preparation examples show a superior action compared to the prior art: 3, 10, 11, 16, 25, 120, 125, 127, 136, 143, 249, 264 and 272.

EXAMPLE H

LD$_{100}$ test

Test animals: *Sitophilus granarius*
Solvent: Acetone.

2 parts by weight of active compound are taken up in 1,000 parts by volume of solvent. The solution thus obtained is diluted with further solvent to the desired concentration.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per m$^2$ of filterpaper varies, depending on the concentration of the active compound solution. The stated number of test animals is then introduced into the Petri dish, and the disk is covered with a glass lid.

The condition of the test animals is checked 3 days after the tests have been set up. The destruction is determined in %. 100% means that all the test animals have been killed; 0% means that none of the test animals have been killed.

In this test, for example, the following compounds from the preparation examples show a superior action compared to the prior art: 3, 10, 11, 12, 16, 17, 18, 24, 25, 27, 28, 29, 30, 31, 49, 61, 120, 125, 127, 136, 143, 249, 264 and 272.

EXAMPLE I

Test with *Lucilia cuprina* larvae (OP-res. Goondiwindi strain)

Emulsifier:
- 35 parts by weight of ethylene glycol monomethyl ether
- 35 parts by weight of nonylphenol polyglycol ether.

To produce a suitable preparative of active compound, three parts by weight of active compound are mixed with seven parts by weight of the abovementioned solvent mixture and the concentrate thus obtained is diluted with water to the particular desired concentration.

About 20 *Lucilia cuprina* res. larvae are introduced into a test tube which contains approx. 1 cm$^3$ of horse muscle and 0.5 ml of the preparation of active compound. After 24 hours, the degree of destruction is determined.

In this test, for example, the following compounds from the preparation examples show a superior action compared with the prior art: 5, 10, 11, 12, 22, 23, 25, 27, 29, 30, 35, 36, 37, 38, 39, 66, 67.

EXAMPLE K

Test with *Boophilus microplus* resistant/OP-resistant Biarra strain

Solvent:
- 35 parts by weight of ethylene glycol monomethyl ether
- 35 parts by weight of nonylphenol polyglycol ether.

To produce a suitable preparation of active compound, three parts by weight of active compound are mixed with seven parts by weight of the solvent mixture indicated above, and the concentrate thus obtained is diluted with water to the desired concentration.

10 adult *Boophilus microplus* res. are immersed for 1 minute in the active compound preparation to be tested. After transfer to plastic beakers and storage in a climatically controlled chamber, the degree of destruction is determined.

In this test, for example, the following compounds from the preparation examples show a superior action compared to the prior art: 5, 10, 11, 12, 23, 25, 27, 36, 37, 38, 39, 66, 67.

EXAMPLE L

Facefly test (*Musca autumnalis*)

Solvent:
- 35 parts by weight of ethylene glycol monomethyl ether
- 35 parts by weight of nonylphenol polyglycol ether To produce a suitable formulation, three parts by weight of active compound are mixed with seven parts of the abovementioned mixture and the emulsion concentrate thus obtained is diluted with water to the particular desired concentration.

10 adult faceflies (*Musca autumnalis*) are introduced into Petri dishes containing filter paper discs of appropriate size which have been impregnated one day before the start of the test with 1 ml of the active compound preparation to be tested. After 3 hours, the degree of destruction is determined in percent, 100% meaning that all of the flies have been destroyed and 0% meaning that no flies have been destroyed.

In this test, for example, the following compounds from the preparation examples show a superior action compared with the prior art: 22, 25, 35, 36 and 38.

EXAMPLE M

Test with *Psoroptes ovis*

Solvent:
- 35 parts by weight of ethylene glycol monomethyl ether
- 35 parts by weight of nonylphenol polyglycol ether.

To produce a suitable preparation of active compound, three parts by weight of active compound are mixed with seven parts by weight of the abovementioned solvent mixture and the concentrate thus obtained is diluted with water to the desired concentration.

About 10–25 *Psoroptes ovis* introduced into 1 ml of the active compound preparation to be tested, these having been pipetted into tablet nests of a deep-drawn package. The degree of destruction is determined after 24 hours.

In this test, for example, the following compounds from the preparation examples show a superior action compared to the prior art: 25, 35, 38, 66 and 67.

EXAMPLE N

Test with parasitic, adult biting flies (*Stomoxys calcitrans*)

Solvent: Cremophor.

To produce a suitable preparation of active compound, the active substance in question is mixed with the stated solvent in a ratio of 1:2 and the concentrate thus obtained is diluted with water to the desired concentration.

10 adult biting flies (*Stomoxys calcitrans*) are introduced into Petri dishes containing sandwiches which have been impregnated one day before the start of the test with 1 ml of the active compound preparation to be tested. After 3 hours, the degree of destruction is determined in percent, 100% meaning that all the flies have been killed and 0% meaning that none of the flies have been killed.

In this test, for example, the following compounds from the preparation examples show a superior action compared to the prior art: 66 and 67.

EXAMPLE P

Nematodes in vitro test

The destruction and inhibition of multiplication of the nematodes *Caenorhabditis elegans* in a liquid medium in the presence of bacteria (*E. coli*), which serve as nutrition for the nematodes, is tested.

The substances to be tested are added to the cultures and the resulting impairment in the multiplication is evaluated as the nematicidal action. The concentration which prevents multiplication is given.

In this test, for example, the following compounds from the preparation examples show at least 95% inhibition of the multiplication of the nematode *C. elegans* at a concentration of $\leq 100$ μg/ml: 5, 7, 8, 10, 12, 13, 14, 15, 16, 17, 18, 19, 23, 25, 27, 28, 29 and 41 at a concentration of $\leq 10$ μg/ml: 30, 36 and 40.

It will be appreciated that the instant specification and claims are set forth by way of illustration and not limitation, and that various modifications and changes may be made without departing from the spirit and scope of the present invention.

We claim:

1. A 5-aminopyrazole of the formula

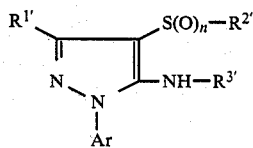

in which
$R^{1'}$ stands for alkyl $(C_1-C_4)$ or halogenoalkyl $(C_1-C_4)$,
$R^{2'}$ stands for alkyl $(C_1-C_8)$ or halogenoalkyl $(C_1-C_8)$,
$R^{3'}$ stands for hydrogen or alkyl $(C_1-C_4)$, n stands for 0, 1 or 2 and
Ar stands for phenyl, 2-pyridyl, 3-pyridyl or 4-pyridyl, said Ar being unsubstituted or monosubstituted or polysubstituted by identical or different substituents selected from the group consisting of cyano, nitro, halogen, straight-chain or branched alkyl with up to 4 carbon atoms, alkoxy with up to 4 carbon atoms and alkoxycarbonyl with up to 4 carbon atoms, straight-chain or branched halogenoalkyl with up to 4 carbon atoms and up to 9 identical or different halogen atoms, and halogenoalkoxy with up to 4 carbon atoms and up to 9 identical or different halogen atoms and a radical $-S(O)_m-R^5$ wherein
$R^5$ represents amino, straight-chain or branched alkyl with up to 4 carbon atoms, alkylamino with up to 4 carbon atoms, dialkylamino with up to 4 carbon atoms, halogenoalkyl with up to 4 carbon atoms and with up to 9 identical or different halogen atoms, and
m represents the number 0, 1 or 2.

2. A 5-aminopyrazole according to claim 1 having the formula

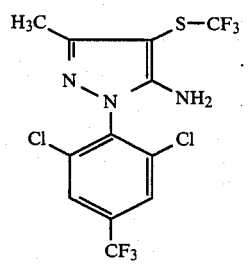

3. A 5-aminopyrazole according to claim 1 having the formula

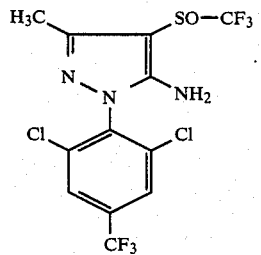

4. A 5-aminopyrazole having the formula

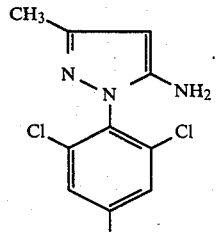

5. A method of combating insects, arachnids and namatodes comprising applying to insects, arachnids and nematodes and/or their environment an effective amount of at least one 5-aminopyrazole of the formula (I)

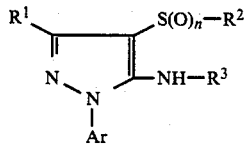

in which
R¹ represents hydrogen, alkyl with 1 to 4 carbon atoms or halogenoalkyl with 1 to 4 carbon atoms,
R² represents alkyl with 1 to 8 carbon atoms, halogenoalkyl with 1 to 8 carbon atoms, unsubstituted or monosubstituted or polysubstituted phenylalkyl, the substituents being identical or different and being halogen, cyano, nitro, straight-chain or branched alkyl, alkoxy, alkythio, alkylsulphonyl, halogenalkyl, halogenoalkylthio, halogenoalkylsulphinyl and halogenoalkylsulphonyl, with in each case 1 to 4 carbon atoms in the alkyl part, or unsubstituted or monosubstituted or polysubstituted phenyl, the substituents being identical or different and being halogen, cyano, nitro, straight-chain or branched alkyl, alkoxy, alkylthio, alkylsulphonyl, halogenalkyl, halogenoalkylthio, halogenoalkylsulphinyl and halogenoalkylsulphonyl, with in each case 1 to 4 carbon atoms in the alkyl part,
R³ represents hydrogen, alkyl with 1 to 4 carbon atoms or a radical

Ar represents unsubstituted phenyl or phenyl monosubstituted or polysubstituted by identical or different substituents selected from the group consisting of cyano, nitro, halogen, straight-chain $C_1$ to $C_4$ alkyl, branched $C_1$ to $C_4$ alkyl, $C_1$ to $C_4$ alkoxy, $C_1$ to $C_4$ alkoxycarbonyl, halogenoalkyl having 1 to 4 carbon atoms, and halogenoalkoxy having 1 to 4 carbon atoms, or unsubstituted pyridyl or pyridyl monosubstituted or polysubstituted by identical or different substituents selected from the group consisting of cyano, nitro, halogen, straight-chain $C_1$ to $C_4$ alkyl, branched $C_1$ to $C_4$ alkyl, $C_1$ to $C_4$ alkoxy, $C_1$ to $C_4$ alkoxycarbonyl, halogenoalkyl having 1 to 4 carbon atoms, and halogenoalkoxy having 1 to 4 carbon atoms, and
n represents the number 0, 1 or 2,
wherein
X represents oxygen or sulphur and
R⁴ represents hydrogen, alkyl with up to 4 carbon atoms, alkenyl with up to 4 carbon atoms, alkinyl with up to 4 carbon atoms, halogenoalkyl with up to 4 carbon atoms, alkoxyalkyl with up to 4 carbon atoms, unsubstituted cycloalkyl having 3 to 7 carbon atoms or cycloalkyl having 3 to 7 carbon atoms and being monosubstituted or polysubstituted by identical or different substituents selected from the group consisting of halogen, lower alkyl and lower halogenoalkyl, alkoxy with up to 4 carbon atoms, alkylamino with up to 4 carbon atoms, dialkylamino with up to 4 carbon atoms or represents phenyl, phenoxy, phenylthio and phenylamino being unsubstituted or monosubstituted or polysubstituted by identical or different substituents, the substituents on the phenyl ring being halogen, cyano, nitro, straight-chain or branched alkyl, alkoxy, alkylthio, alkylsulphinyl and alkylsulphonyl, with in each case 1 to 4 carbon atoms in the individual alkyl parts.

6. A method according to claim 5, wherein in the formula I,
R¹ represents straight-chain or branched alkyl with 1 to 4 carbon atoms or straight-chain or branched halogenoalkyl with 1 to 4 carbon atoms, or represents hydrogen,
R² represents straight-chain or branched alkyl with 1 to 8 carbon atoms or straight-chain or branched halogenoalkyl with 1 to 8 carbon atoms, or represents phenyl or phenylalkyl with 1 to 4 carbon atoms in the straight-chain or branched alkyl part and said phenyl or phenylalkyl being unsubstituted or monosubstituted or polysubstituted by identical or different substituents, the substituents on the phenyl part being halogen, cyano, nitro or the substituents being straight-chain or branched alkyl, alkoxy, alkylthio, alkylsulphinyl, alkylsulphonyl, halogenoalkyl, halogenoalkoxy, halogenoalkylthio, halogenoalkylsulphinyl and halogenoalkylsulphonyl, with in each case 1 to 4 carbon atoms in the individual alkyl parts, R³ represents hydrogen, straight-chain or branched alkyl with 1 to 4 carbon atoms or a radical

wherein
X represents oxygen or sulphur and
R⁴ represents hydrogen, or represents straight-chain or branched alkyl with up to 4 carbon atoms, straight-chain or branched alkenyl with up to 4 carbon atoms, straight-chain or branched alkinyl with up to 4 carbon atoms, straight-chain or branched alkoxyalkyl with up to 4 carbon atoms, straight-chain or branched alkylthioalkyl with up to 4 carbon atoms, straight-chain or branched alkoxy with up to 4 carbon atoms, straight-chain or branched alkylthio with up to 4 carbon atoms, straight-chain or branched alkylamino with up to 4 carbon atoms, straight-chain or branched dialkylamino with up to 4 carbon atoms or straight-chain or branched halogenoalkyl with up to 4 carbon atoms in the alkyl part, the halogenoalkyl having up to 9 identical or different halogen atoms, or represents cycloalkyl which has 3 to 7 carbon atoms and unsubstituted or monosubstituted or polysubstituted by identical or different substituents selected from the group consisting of halogen, lower alkyl and lower halogenoalkyl, or represents phenyl, phenoxy, phenylthio or phenylamino, the phenyl, phenoxy, phenylthio and phenylamino being unsubstituted or monosubstituted or polysubstituted by identical or different substituents, the substituents on the phenyl being halogen, cyano, nitro, straight-chain or branched alkyl, alkoxy, alkylthio, alkylsulphinyl, and alkylsulphonyl with in each case, 1 to 4 carbon atoms in the individual alkyl parts, Ar represents phenyl, 2-pyridyl, 3-pyridyl or 4-pyridyl, said phenyl, 2-pyridyl, 3-pyridyl and 4-pyridyl being unsubstituted or monosubstituted or polysubstituted by identical or different substituents, the substituents being cyano, nitro, halogen, straight-chain or branched alkyl with up to 4 carbon atoms, straight-chain or branched alkoxy with up to 4 carbon atoms, straight-chain or branched alkoxycarbonyl with up to 4 carbon atoms, straight chain or branched halogenoalkyl with up to 4 carbon atoms and up to 9 identical or different halogen atoms or straight-chain or branched halogenoalkoxy with up to 4 carbon atoms and up to 9 identical or different halogen atoms, or represents a radical —S(O)$_m$—R$^5$ wherein R$^5$ represents amino, or represents straight-chain or branched alkyl with up to 4 carbon atoms, straight-chain or branched alkylamino with up to 4 carbon atoms, straight-chain or branched dialkylamino with up to 4 carbon atoms or straight-chain or branched halogenoalkyl with up to 4 carbon atoms, the halogenoalkyl having 1 to 9 identical or different halogen atoms, m represents the number 0, 1 or 2, and n represents the number, 0, 1 or 2.

7. A method according to claim 6, wherein in the formula I for R$^1$, the halogenoalkyl has 1 to 9 identical or different halogen atoms; wherein in the formula I, for R$^2$, the halogenoalkyl has 1 to 17 identical or different halogen atoms; and wherein in the formula I, for R$^2$, the halogenoalkylsulphinyl and/or the halogenoalkylsulphonyl has 1 to 9 identical or different halogen atoms.

8. A method according to claim 5, wherein the 5-aminopyrazole is selected from the group consisting of

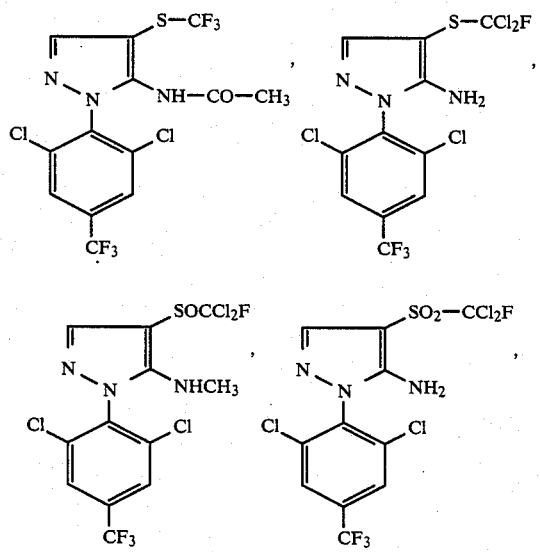

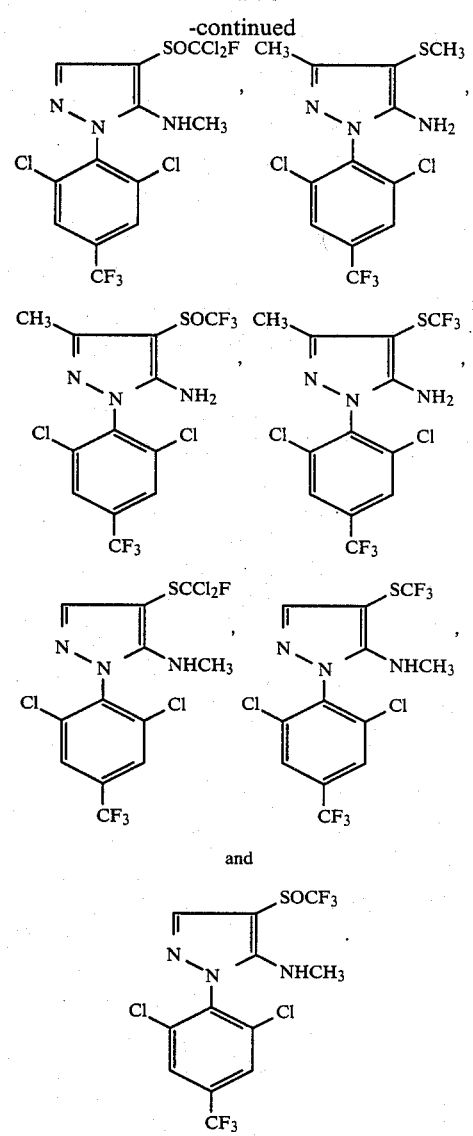

and

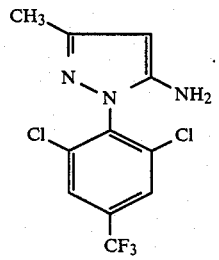

9. A method of combating insects, arachnids and namatodes comprising applying an effective amount of the 5-aminopyrazole according to claim 1 to insects, arachnids and nematodes and/or their environment.

10. A method of combating insects, sense animals and nematodes comprising applying to insects, arachnids and nematodes and/or their environment an effective amount of a 5-aminopyrazole of the formula 11. An insecticidal, araricidal and nematicidal composition comprising an effective amount of a compound according to claim 1 in admixture with one or more extenders and/or one or more surface active agents.

UNITED STATES PATENT AND TRADEMARK OFFICE
CERTIFICATE OF CORRECTION

PATENT NO. : 4,804,675

DATED : February 14, 1989

INVENTOR(S) : Jensen-Korte et al

It is certified that error appears in the above-identified patent and that said Letters Patent is hereby corrected as shown below:

| | |
|---|---|
| Title Page, Title, line 1 | Correct --ALKYLTHIO-PYRAZOL- -- |
| Col. 27, line 22 | After "20" second instance delete "+" and substitute --°-- |
| Col. 30, lines 41-42 | Delete "diethylacetamide" and substitute --dimethylacetamide-- |
| Col. 31, line 30 | Delete "Solvent" and substitute --Solvents-- |
| Col. 31, line 31 | Delete "hexene" and substitute --hexane-- |
| Col. 39, line 17 | Delete "relux" and substitute --reflux-- |
| Col. 63, Example No. 112, under "$R^2$" | Delete "$CClF_2$" and substitute --$CCl_2F$-- |
| Col. 95, Example No. 245, under "$R^3$" | Delete "H" and substitute --$CH_3$-- |
| Col. 112, line 64 | Before "weight" delete "of" and substitute --by-- |
| Col. 115, line 45 | Delete "disk" and substitute --dish-- |
| Col. 117, lines 48, 50 | Delete "$\leqq$" and substitute --$\leq$-- |

Signed and Sealed this

Ninth Day of January, 1990

Attest:

JEFFREY M. SAMUELS

Attesting Officer     Acting Commissioner of Patents and Trademarks